(12) United States Patent
Jodaitis et al.

(10) Patent No.: US 8,465,546 B2
(45) Date of Patent: Jun. 18, 2013

(54) INTERVERTEBRAL DISC PROSTHESIS INSERTION ASSEMBLIES

(75) Inventors: Alexandre Jodaitis, Morlanwelz (BE); Herve Dinville, St-Parres-aux-Tertres (FR); Alexis Mercier, Troyes (FR)

(73) Assignee: LDR Medical, Rosières Près Troyes (FR)

( * ) Notice: Subject to any disclaimer, the term of this patent is extended or adjusted under 35 U.S.C. 154(b) by 872 days.

(21) Appl. No.: 11/676,237

(22) Filed: Feb. 16, 2007

(65) Prior Publication Data

US 2008/0200984 A1    Aug. 21, 2008

(51) Int. Cl.
*A61F 2/44* (2006.01)

(52) U.S. Cl.
USPC ........................................... 623/17.16

(58) Field of Classification Search
USPC ................................ 606/99; 623/17.11–17.16
See application file for complete search history.

(56) References Cited

U.S. PATENT DOCUMENTS

| | | |
|---|---|---|
| 566,360 A | 8/1896 | White |
| 1,436,573 A | 11/1922 | Choppinet et al. |
| 2,836,442 A | 5/1958 | Moskovitz |
| 3,325,197 A | 6/1967 | Wehner |
| 3,374,786 A | 3/1968 | Callender et al. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |

(Continued)

FOREIGN PATENT DOCUMENTS

| | | |
|---|---|---|
| CA | 2472708 | 2/2005 |
| CA | 2533473 | 3/2011 |

(Continued)

OTHER PUBLICATIONS

A biological basis for instantaneous centres of rotation of the vertebral column, N. Bouduk, B. Amevo, M. Pearcy, Proc Institution Mechanical Engineers, Jun. 16, 1995, pp. 177-183.

(Continued)

*Primary Examiner* — Eduardo C Robert
*Assistant Examiner* — Steven Cotroneo
(74) *Attorney, Agent, or Firm* — Denko Coburn & Lauff LLP

(57) ABSTRACT

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various other embodiments, the prosthesis and an insertion tool are provided in a sterile pack, with the prosthesis components and the insertion tool sterilized and packaged in one or more types or layers of sterile packaging.

13 Claims, 11 Drawing Sheets

U.S. PATENT DOCUMENTS

| | | |
|---|---|---|
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-Janz et al. |
| 4,759,769 A | 7/1988 | Hedman et al. |
| 4,787,378 A | 11/1988 | Sodhi |
| 4,787,908 A | 11/1988 | Wyss et al. |
| 4,790,303 A | 12/1988 | Steffee |
| 4,791,918 A | 12/1988 | Von Hasselbach |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,911,718 A | 3/1990 | Lee et al. |
| 4,932,975 A | 6/1990 | Main |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,290,312 A | 3/1994 | Kojimoto et al. |
| 5,300,074 A | 4/1994 | Frigg |
| 5,306,309 A * | 4/1994 | Wagner et al. ............ 623/17.16 |
| 5,314,477 A | 5/1994 | Marnay |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buttner-Janz et al. |
| 5,417,692 A | 5/1995 | Goble et al. |
| 5,417,712 A | 5/1995 | Whittaker et al. |
| 5,425,773 A | 6/1995 | Boyd et al. |
| 5,429,641 A | 7/1995 | Gotfried |
| 5,437,674 A | 8/1995 | Worcel et al. |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buttner-Janz et al. |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | McDevitt |
| 5,645,596 A | 7/1997 | Kim |
| 5,655,698 A | 8/1997 | Yoon et al. |
| 5,674,294 A | 10/1997 | Bainville et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,702,449 A | 12/1997 | McKay |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,807,403 A | 9/1998 | Beyar et al. |
| 5,824,094 A | 10/1998 | Serhan et al. |
| 5,827,328 A | 10/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,968,098 A | 10/1999 | Winslow |
| 5,980,522 A | 11/1999 | Koros et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |

| | | |
|---|---|---|
| 6,045,552 A | 4/2000 | Zucherman et al. |
| 6,063,088 A | 5/2000 | Winslow |
| 6,063,121 A | 5/2000 | Xavier et al. |
| 6,066,175 A | 5/2000 | Henderson et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,113,637 A | 9/2000 | Gill et al. |
| 6,113,638 A | 9/2000 | Williams et al. |
| 6,129,763 A | 10/2000 | Chauvin et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,241,769 B1 | 6/2001 | Nicholson et al. |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,342,074 B1 | 1/2002 | Simpson |
| 6,344,057 B1 | 2/2002 | Rabbe et al. |
| 6,364,880 B1 | 4/2002 | Michelson |
| 6,368,350 B1 | 4/2002 | Erickson et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,485,517 B1 | 11/2002 | Michelson |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,558,423 B1 | 5/2003 | Michelson |
| 6,558,424 B1 | 5/2003 | Thalgott |
| 6,565,605 B2 | 5/2003 | Goble et al. |
| 6,572,653 B1 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet et al. |
| 6,592,624 B1 | 7/2003 | Fraser et al. |
| 6,599,320 B1 | 7/2003 | Kuslich et al. |
| 6,607,530 B1 | 8/2003 | Carl et al. |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,709,458 B2 | 3/2004 | Michelson |
| 6,716,247 B2 | 4/2004 | Michelson |
| 6,719,794 B2 | 4/2004 | Gerber et al. |
| 6,723,127 B2 | 4/2004 | Ralph et al. |
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,749,636 B2 | 6/2004 | Michelson |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,678 B2 | 9/2004 | Hawkins |
| 6,793,679 B2 | 9/2004 | Michelson |
| 6,800,093 B2 | 10/2004 | Nicholson et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |

| | | | | | | |
|---|---|---|---|---|---|---|
| 6,962,606 B2 | 11/2005 | Michelson | | 7,632,282 B2 | 12/2009 | Dinville |
| 6,964,686 B2 | 11/2005 | Gordon | | 7,637,951 B2 | 12/2009 | Michelson |
| 6,966,929 B2 | 11/2005 | Mitchell | | 7,637,954 B2 | 12/2009 | Michelson |
| 6,972,019 B2 | 12/2005 | Michelson | | 7,641,690 B2 | 1/2010 | Abdou |
| 6,972,035 B2 | 12/2005 | Michelson | | 7,655,027 B2 | 2/2010 | Michelson |
| 6,981,975 B2 | 1/2006 | Michelson | | 7,658,766 B2 | 2/2010 | Melkent et al. |
| 6,984,234 B2 | 1/2006 | Bray | | 7,682,396 B2 | 3/2010 | Beaurain et al. |
| 6,984,245 B2 | 1/2006 | McGahan et al. | | 7,695,516 B2 | 4/2010 | Zeegers |
| 6,986,789 B2 | 1/2006 | Schultz et al. | | 7,695,517 B2 | 4/2010 | Benzel et al. |
| 6,994,727 B2 | 2/2006 | Khandkar et al. | | 7,695,518 B2 | 4/2010 | Gau |
| 7,001,385 B2 | 2/2006 | Bonutti | | 7,727,280 B2 | 6/2010 | McLuen |
| 7,001,432 B2 | 2/2006 | Keller et al. | | 7,749,252 B2 | 7/2010 | Zucherman et al. |
| 7,008,453 B1 | 3/2006 | Michelson | | 7,749,274 B2 | 7/2010 | Razian |
| 7,011,684 B2 | 3/2006 | Eckman | | 7,753,937 B2 | 7/2010 | Chervitz et al. |
| 7,025,787 B2 | 4/2006 | Bryan et al. | | 7,771,473 B2 | 8/2010 | Thramann |
| 7,033,394 B2 | 4/2006 | Michelson | | 7,771,475 B2 | 8/2010 | Michelson |
| 7,037,340 B2 | 5/2006 | Gau | | 7,776,090 B2 | 8/2010 | Winslow et al. |
| 7,041,135 B2 | 5/2006 | Michelson | | 7,780,670 B2 | 8/2010 | Bonutti |
| 7,041,136 B2 | 5/2006 | Goble et al. | | 7,789,914 B2 | 9/2010 | Michelson |
| 7,056,344 B2 | 6/2006 | Huppert et al. | | 7,794,502 B2 | 9/2010 | Michelson |
| 7,060,097 B2 | 6/2006 | Fraser et al. | | 7,799,053 B2 | 9/2010 | Haid, Jr. et al. |
| 7,060,099 B2 | 6/2006 | Carli et al. | | 7,799,057 B2 | 9/2010 | Hudgins et al. |
| 7,063,701 B2 | 6/2006 | Michelson | | 7,799,081 B2 | 9/2010 | McKinley |
| 7,063,702 B2 | 6/2006 | Michelson | | 7,811,326 B2 | 10/2010 | Braddock, Jr. et al. |
| 7,066,961 B2 | 6/2006 | Michelson | | 7,819,903 B2 | 10/2010 | Fraser et al. |
| 7,074,237 B2 | 7/2006 | Goble et al. | | 7,824,445 B2 | 11/2010 | Biro et al. |
| 7,090,698 B2 | 8/2006 | Goble et al. | | 7,833,255 B2 | 11/2010 | Chow et al. |
| 7,094,239 B1 | 8/2006 | Michelson | | 7,842,088 B2 | 11/2010 | Rashbaum et al. |
| 7,105,023 B2 | 9/2006 | Eckman | | 7,846,207 B2 | 12/2010 | Lechmann et al. |
| 7,105,024 B2 | 9/2006 | Richelsoph | | 7,850,731 B2 | 12/2010 | Brittan et al. |
| 7,112,206 B2 | 9/2006 | Michelson | | 7,850,732 B2 | 12/2010 | Heinz |
| 7,118,579 B2 | 10/2006 | Michelson | | 7,850,733 B2 | 12/2010 | Baynham et al. |
| 7,118,580 B1 | 10/2006 | Beyersdorff et al. | | 7,862,616 B2 | 1/2011 | Lechmann et al. |
| 7,118,598 B2 | 10/2006 | Michelson | | 7,871,441 B2 | 1/2011 | Eckman |
| 7,128,760 B2 | 10/2006 | Michelson | | 7,875,076 B2 | 1/2011 | Mathieu et al. |
| 7,128,761 B2 | 10/2006 | Kuras et al. | | 7,887,591 B2 | 2/2011 | Aebi et al. |
| 7,153,325 B2 | 12/2006 | Kim et al. | | 7,892,261 B2 | 2/2011 | Bonutti |
| 7,163,561 B2 | 1/2007 | Michelson | | 7,892,286 B2 | 2/2011 | Michelson |
| 7,169,153 B2 | 1/2007 | Keller | | 7,909,871 B2 | 3/2011 | Abdou |
| 7,175,662 B2 | 2/2007 | Link et al. | | 7,914,560 B2 | 3/2011 | Hoy et al. |
| 7,179,294 B2 | 2/2007 | Eisermann et al. | | 7,922,729 B2 | 4/2011 | Michelson |
| 7,198,644 B2 | 4/2007 | Schultz et al. | | 7,931,674 B2 | 4/2011 | Zucherman et al. |
| 7,204,851 B2 | 4/2007 | Trieu et al. | | 7,931,840 B2 | 4/2011 | Michelson |
| 7,204,852 B2 | 4/2007 | Marnay et al. | | 7,935,149 B2 | 5/2011 | Michelson |
| 7,211,112 B2 | 5/2007 | Baynham et al. | | 7,951,198 B2 | 5/2011 | Sucec et al. |
| 7,217,291 B2 | 5/2007 | Zucherman et al. | | 7,955,390 B2 | 6/2011 | Fallin et al. |
| 7,217,292 B2 | 5/2007 | Ralph et al. | | 7,972,337 B2 | 7/2011 | Boyajian et al. |
| 7,217,293 B2 | 5/2007 | Branch, Jr. | | 7,972,363 B2 | 7/2011 | Moskowitz et al. |
| 7,223,289 B2 | 5/2007 | Trieu et al. | | 7,972,365 B2 | 7/2011 | Michelson |
| 7,232,463 B2 | 6/2007 | Falahee | | 7,976,566 B2 | 7/2011 | Michelson |
| 7,232,464 B2 | 6/2007 | Mathieu et al. | | 7,985,255 B2 | 7/2011 | Bray et al. |
| 7,291,170 B2 | 11/2007 | Huppert | | 7,985,258 B2 | 7/2011 | Zdeblick et al. |
| 7,326,248 B2 | 2/2008 | Michelson | | 7,993,373 B2 | 8/2011 | Hoy et al. |
| 7,326,250 B2 | 2/2008 | Beaurain et al. | | 7,998,177 B2 | 8/2011 | Hoy et al. |
| 7,410,501 B2 | 8/2008 | Michelson | | 7,998,178 B2 | 8/2011 | Hoy et al. |
| 7,419,505 B2 * | 9/2008 | Fleischmann et al. ..... 623/17.11 | | 7,998,211 B2 | 8/2011 | Baccelli et al. |
| 7,431,735 B2 | 10/2008 | Liu et al. | | 8,002,835 B2 | 8/2011 | Zeegers |
| 7,435,262 B2 | 10/2008 | Michelson | | 8,007,534 B2 | 8/2011 | Michelson |
| 7,442,209 B2 | 10/2008 | Michelson | | 8,021,401 B2 | 9/2011 | Carl et al. |
| 7,445,635 B2 | 11/2008 | Fallin et al. | | 8,021,430 B2 | 9/2011 | Michelson |
| 7,445,636 B2 | 11/2008 | Michelson | | 8,043,334 B2 | 10/2011 | Fisher et al. |
| 7,455,692 B2 | 11/2008 | Michelson | | 8,062,336 B2 | 11/2011 | Triplett et al. |
| 7,465,317 B2 | 12/2008 | Malberg et al. | | 8,062,375 B2 | 11/2011 | Glerum et al. |
| 7,494,508 B2 | 2/2009 | Zeegers | | 8,066,741 B2 | 11/2011 | Fallin et al. |
| 7,503,933 B2 | 3/2009 | Michelson | | 8,066,749 B2 | 11/2011 | Winslow et al. |
| 7,507,248 B2 | 3/2009 | Beaurain et al. | | 8,070,816 B2 | 12/2011 | Taylor |
| 7,540,882 B2 | 6/2009 | Michelson | | 8,070,819 B2 | 12/2011 | Aferzon et al. |
| 7,566,345 B1 | 7/2009 | Fallin et al. | | 8,075,593 B2 | 12/2011 | Hess |
| 7,588,590 B2 | 9/2009 | Chervitz et al. | | 8,075,618 B2 | 12/2011 | Trieu et al. |
| 7,591,851 B2 | 9/2009 | Winslow et al. | | 8,075,621 B2 | 12/2011 | Michelson |
| 7,594,931 B2 | 9/2009 | Louis et al. | | 8,114,082 B2 | 2/2012 | Boyajian et al. |
| 7,594,932 B2 | 9/2009 | Aferzon et al. | | 8,147,556 B2 | 4/2012 | Louis et al. |
| 7,601,170 B2 | 10/2009 | Winslow et al. | | 8,162,988 B2 | 4/2012 | Delecrin et al. |
| 7,608,107 B2 | 10/2009 | Michelson | | 2001/0020185 A1 | 9/2001 | Ray |
| 7,618,453 B2 | 11/2009 | Goble et al. | | 2002/0040243 A1 | 4/2002 | Attali et al. |
| 7,618,455 B2 | 11/2009 | Goble et al. | | 2002/0087212 A1 | 7/2002 | James et al. |
| 7,618,456 B2 | 11/2009 | Mathieu et al. | | 2002/0143343 A1 | 10/2002 | Castro |
| 7,621,955 B2 | 11/2009 | Goble et al. | | 2002/0161444 A1 | 10/2002 | Choi |
| 7,621,958 B2 | 11/2009 | Zdeblick et al. | | 2002/0165613 A1 | 11/2002 | Lin et al. |

| | | | | | | |
|---|---|---|---|---|---|---|
| 2002/0193880 A1 | 12/2002 | Fraser | | 2005/0131542 A1 | 6/2005 | Benzel et al. |
| 2003/0028249 A1 | 2/2003 | Baccelli et al. | | 2005/0131544 A1 | 6/2005 | Kuras et al. |
| 2003/0055503 A1 | 3/2003 | O'Neil | | 2005/0143733 A1 | 6/2005 | Petit |
| 2003/0069586 A1 | 4/2003 | Errico et al. | | 2005/0143824 A1 | 6/2005 | Richelsoph et al. |
| 2003/0074075 A1 | 4/2003 | Thomas, Jr. et al. | | 2005/0143825 A1 | 6/2005 | Enayati |
| 2003/0093153 A1 | 5/2003 | Banick et al. | | 2005/0149189 A1 | 7/2005 | Mokhtar et al. |
| 2003/0093156 A1 | 5/2003 | Metzger et al. | | 2005/0154462 A1 | 7/2005 | Zucherman et al. |
| 2003/0109928 A1 | 6/2003 | Pasquet et al. | | 2005/0159818 A1 | 7/2005 | Blain |
| 2003/0135279 A1 | 7/2003 | Michelson | | 2005/0165408 A1 | 7/2005 | Puno et al. |
| 2003/0149438 A1 | 8/2003 | Nichols et al. | | 2005/0165485 A1 | 7/2005 | Trieu |
| 2003/0171814 A1 | 9/2003 | Muhanna et al. | | 2005/0171610 A1 | 8/2005 | Humphreys et al. |
| 2003/0187436 A1 | 10/2003 | Bolger et al. | | 2005/0192671 A1 | 9/2005 | Bao et al. |
| 2003/0187506 A1 | 10/2003 | Ross et al. | | 2005/0197705 A1 | 9/2005 | Arnin et al. |
| 2003/0195514 A1 | 10/2003 | Trieu et al. | | 2005/0197706 A1* | 9/2005 | Hovorka et al. ............ 623/17.15 |
| 2003/0220691 A1 | 11/2003 | Songer et al. | | 2005/0216086 A1 | 9/2005 | Marik et al. |
| 2003/0233145 A1 | 12/2003 | Landry et al. | | 2005/0216092 A1 | 9/2005 | Marik et al. |
| 2004/0002758 A1 | 1/2004 | Landry et al. | | 2005/0228500 A1 | 10/2005 | Kim et al. |
| 2004/0002761 A1 | 1/2004 | Rogers et al. | | 2005/0234553 A1 | 10/2005 | Gordon |
| 2004/0010312 A1 | 1/2004 | Enayati | | 2005/0240273 A1 | 10/2005 | Khandkar et al. |
| 2004/0010316 A1 | 1/2004 | William et al. | | 2005/0246024 A1 | 11/2005 | Zeegers |
| 2004/0024406 A1* | 2/2004 | Ralph et al. ............... 606/90 | | 2005/0251260 A1 | 11/2005 | Gerber et al. |
| 2004/0030387 A1 | 2/2004 | Landry et al. | | 2005/0256579 A1 | 11/2005 | Keller et al. |
| 2004/0034423 A1 | 2/2004 | Lyons et al. | | 2005/0267581 A1 | 12/2005 | Marnay et al. |
| 2004/0073309 A1 | 4/2004 | Bianchi et al. | | 2005/0273171 A1 | 12/2005 | Gordon et al. |
| 2004/0073311 A1 | 4/2004 | Ferree | | 2005/0273173 A1 | 12/2005 | Gordon et al. |
| 2004/0083000 A1 | 4/2004 | Keller et al. | | 2005/0273174 A1 | 12/2005 | Gordon et al. |
| 2004/0093082 A1 | 5/2004 | Ferree | | 2005/0273175 A1 | 12/2005 | Gordon et al. |
| 2004/0093083 A1 | 5/2004 | Branch et al. | | 2005/0278026 A1 | 12/2005 | Gordon et al. |
| 2004/0102846 A1 | 5/2004 | Keller et al. | | 2005/0283242 A1 | 12/2005 | Zucherman et al. |
| 2004/0111160 A1 | 6/2004 | Evans et al. | | 2005/0283244 A1 | 12/2005 | Gordon et al. |
| 2004/0117022 A1 | 6/2004 | Marnay et al. | | 2005/0283245 A1 | 12/2005 | Gordon et al. |
| 2004/0133278 A1 | 7/2004 | Marino et al. | | 2005/0283247 A1 | 12/2005 | Gordon et al. |
| 2004/0133281 A1 | 7/2004 | Khandkar et al. | | 2005/0283248 A1 | 12/2005 | Gordon et al. |
| 2004/0143332 A1 | 7/2004 | Krueger et al. | | 2006/0015183 A1 | 1/2006 | Gilbert et al. |
| 2004/0148029 A1 | 7/2004 | Bianchi et al. | | 2006/0016768 A1 | 1/2006 | Grichar et al. |
| 2004/0153157 A1 | 8/2004 | Keller | | 2006/0020341 A1 | 1/2006 | Schneid et al. |
| 2004/0158254 A1 | 8/2004 | Eisermann | | 2006/0030860 A1* | 2/2006 | Peterman ................ 606/99 |
| 2004/0158328 A1 | 8/2004 | Eisermann | | 2006/0036261 A1 | 2/2006 | McDonnell |
| 2004/0162617 A1 | 8/2004 | Zucherman et al. | | 2006/0036325 A1 | 2/2006 | Paul et al. |
| 2004/0172020 A1 | 9/2004 | Beaurain et al. | | 2006/0036326 A1 | 2/2006 | Baumgartner et al. |
| 2004/0193273 A1 | 9/2004 | Huang | | 2006/0041313 A1 | 2/2006 | Allard et al. |
| 2004/0199254 A1 | 10/2004 | Louis et al. | | 2006/0041314 A1 | 2/2006 | Millard |
| 2004/0210219 A1 | 10/2004 | Bray | | 2006/0058878 A1 | 3/2006 | Michelson |
| 2004/0210313 A1 | 10/2004 | Michelson | | 2006/0069437 A1 | 3/2006 | Weber |
| 2004/0220582 A1 | 11/2004 | Keller | | 2006/0069441 A1 | 3/2006 | Zucherman et al. |
| 2004/0225295 A1 | 11/2004 | Zubok et al. | | 2006/0085076 A1 | 4/2006 | Krishna et al. |
| 2004/0225363 A1 | 11/2004 | Richelsoph | | 2006/0085077 A1 | 4/2006 | Cook et al. |
| 2004/0225364 A1 | 11/2004 | Richelsoph | | 2006/0089717 A1 | 4/2006 | Krishna et al. |
| 2004/0243238 A1 | 12/2004 | Arnin et al. | | 2006/0095136 A1 | 5/2006 | McLuen |
| 2004/0243240 A1 | 12/2004 | Beaurain et al. | | 2006/0111783 A1 | 5/2006 | Aflatoon et al. |
| 2004/0254577 A1 | 12/2004 | Delecrin et al. | | 2006/0116768 A1* | 6/2006 | Krueger et al. ............ 623/17.14 |
| 2004/0254643 A1 | 12/2004 | Jackson | | 2006/0116769 A1 | 6/2006 | Marnay et al. |
| 2005/0010215 A1 | 1/2005 | Delecrin et al. | | 2006/0122703 A1 | 6/2006 | Aebi et al. |
| 2005/0015094 A1 | 1/2005 | Keller | | 2006/0129244 A1 | 6/2006 | Ensign |
| 2005/0015095 A1 | 1/2005 | Keller | | 2006/0136063 A1 | 6/2006 | Zeegers |
| 2005/0015149 A1 | 1/2005 | Michelson | | 2006/0142863 A1 | 6/2006 | Fraser et al. |
| 2005/0021042 A1 | 1/2005 | Marnay et al. | | 2006/0149273 A1 | 7/2006 | Ross et al. |
| 2005/0027359 A1 | 2/2005 | Mashburn | | 2006/0149371 A1 | 7/2006 | Marik et al. |
| 2005/0027363 A1 | 2/2005 | Gordon | | 2006/0149378 A1 | 7/2006 | Chase et al. |
| 2005/0033305 A1 | 2/2005 | Schultz | | 2006/0155377 A1 | 7/2006 | Beaurain et al. |
| 2005/0033428 A1 | 2/2005 | Keller | | 2006/0155378 A1 | 7/2006 | Eckman |
| 2005/0033435 A1 | 2/2005 | Belliard et al. | | 2006/0173544 A1 | 8/2006 | Gau |
| 2005/0033437 A1 | 2/2005 | Bao et al. | | 2006/0178745 A1 | 8/2006 | Bartish, Jr. et al. |
| 2005/0033438 A1 | 2/2005 | Schultz | | 2006/0178746 A1 | 8/2006 | Bartish, Jr. et al. |
| 2005/0038512 A1 | 2/2005 | Michelson | | 2006/0190082 A1 | 8/2006 | Keller et al. |
| 2005/0043798 A1 | 2/2005 | Eckman | | 2006/0200241 A1 | 9/2006 | Rothman et al. |
| 2005/0043800 A1 | 2/2005 | Paul et al. | | 2006/0200242 A1 | 9/2006 | Rothman et al. |
| 2005/0043804 A1 | 2/2005 | Gordon et al. | | 2006/0200243 A1 | 9/2006 | Rothman et al. |
| 2005/0049590 A1 | 3/2005 | Alleyne et al. | | 2006/0206208 A1 | 9/2006 | Michelson |
| 2005/0060034 A1 | 3/2005 | Berry et al. | | 2006/0212123 A1 | 9/2006 | Lechmann et al. |
| 2005/0060037 A1 | 3/2005 | Michelson | | 2006/0235520 A1 | 10/2006 | Pannu |
| 2005/0065608 A1 | 3/2005 | Michelson | | 2006/0235526 A1 | 10/2006 | Lemaire |
| 2005/0065611 A1 | 3/2005 | Huppert et al. | | 2006/0241764 A1 | 10/2006 | Michelson |
| 2005/0071009 A1 | 3/2005 | Muhanna et al. | | 2006/0253201 A1 | 11/2006 | McLuen |
| 2005/0085911 A1 | 4/2005 | Link | | 2006/0259143 A1 | 11/2006 | Navarro et al. |
| 2005/0085917 A1 | 4/2005 | Marnay et al. | | 2006/0265072 A1 | 11/2006 | Richelsoph |
| 2005/0107788 A1 | 5/2005 | Beaurain et al. | | 2006/0282074 A1 | 12/2006 | Renaud et al. |
| 2005/0113926 A1 | 5/2005 | Zucherman et al. | | 2006/0287728 A1 | 12/2006 | Mokhtar et al. |
| 2005/0119665 A1 | 6/2005 | Keller | | 2007/0010886 A1 | 1/2007 | Banick et al. |

| | | |
|---|---|---|
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1* | 4/2007 | Bonutti et al. ............. 606/99 |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1* | 7/2007 | Rashbaum et al. ........ 623/17.11 |
| 2007/0179623 A1 | 8/2007 | Trieu et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1* | 10/2008 | Ralph et al. ............ 606/99 |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |

FOREIGN PATENT DOCUMENTS

| | | |
|---|---|---|
| DE | 2263842 A | 7/1974 |
| DE | 2804936 | 8/1979 |
| DE | 3023353 A | 4/1981 |
| DE | 8912648 U | 11/1990 |
| DE | 4328690 | 3/1995 |
| DE | 29911422 | 8/1999 |
| DE | 20310432 U | 9/2003 |
| DE | 20310433 U | 9/2003 |
| DE | 20320454 | 10/2004 |
| DE | 10323363 | 12/2004 |
| DE | 102004027985 | 7/2005 |
| EP | 42271 | 12/1981 |
| EP | 176728 | 4/1986 |
| EP | 0298235 A | 1/1989 |
| EP | 0317972 A | 5/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |

| | | |
|---|---|---|
| EP | 0637439 | 2/1995 |
| EP | 0697200 | 2/1996 |
| EP | 0566810 B1 | 5/1996 |
| EP | 0738504 | 10/1996 |
| EP | 0747025 A1 | 12/1996 |
| EP | 0852934 | 7/1998 |
| EP | 0903126 | 3/1999 |
| EP | 0951879 | 10/1999 |
| EP | 0955021 A | 11/1999 |
| EP | 0978258 | 2/2000 |
| EP | 1222903 | 7/2002 |
| EP | 125898 A1 | 10/2002 |
| EP | 1287795 | 3/2003 |
| EP | 1344506 | 9/2003 |
| EP | 1344508 | 9/2003 |
| EP | 1374808 | 12/2005 |
| EP | 1504733 B1 | 6/2007 |
| FR | 2124815 A | 9/1972 |
| FR | 2372622 | 6/1978 |
| FR | 2632516 A | 2/1989 |
| FR | 2659226 A | 9/1991 |
| FR | 2716619 | 9/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 A | 2/1997 |
| FR | 2787019 | 12/1998 |
| FR | 2787021 A | 6/2000 |
| FR | 2824261 | 11/2002 |
| FR | 2831796 | 5/2003 |
| FR | 2843293 | 2/2004 |
| FR | 2846550 | 5/2004 |
| FR | 2865530 A1 | 8/2005 |
| FR | 2865629 | 8/2005 |
| FR | 26869528 | 11/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| JP | 2261466 | 10/1990 |
| WO | WO9011740 | 10/1990 |
| WO | WO9011740 A | 10/1990 |
| WO | WO9107931 | 6/1991 |
| WO | WO9113598 A | 9/1991 |
| WO | WO9301771 A | 2/1993 |
| WO | WO9404100 | 3/1994 |
| WO | WO9515133 A1 | 6/1995 |
| WO | WO9817209 | 4/1998 |
| WO | WO9909914 | 3/1999 |
| WO | WO9953871 | 10/1999 |
| WO | WO9956675 A | 11/1999 |
| WO | WO9956676 | 11/1999 |
| WO | WO9965412 | 12/1999 |
| WO | WO9966864 | 12/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO0141680 | 6/2001 |
| WO | WO0143620 | 6/2001 |
| WO | WO0162191 | 8/2001 |
| WO | WO0213732 | 2/2002 |
| WO | WO02058599 | 8/2002 |
| WO | WO02071960 | 9/2002 |
| WO | WO02089701 A2 | 11/2002 |
| WO | WO03005939 | 1/2003 |
| WO | WO03015646 | 2/2003 |
| WO | WO03026522 A2 | 4/2003 |
| WO | WO03039400 A2 | 5/2003 |
| WO | WO03045262 | 6/2003 |
| WO | WO03059212 A | 7/2003 |
| WO | WO03075803 | 9/2003 |
| WO | WO03075804 A | 9/2003 |
| WO | WO2004034935 | 4/2004 |
| WO | WO2004039291 | 5/2004 |
| WO | WO2004041129 A1 | 5/2004 |
| WO | WO2004041131 | 5/2004 |
| WO | WO2004071360 | 8/2004 |
| WO | WO2004089256 | 10/2004 |
| WO | WO2005007040 | 1/2005 |
| WO | WO2005046534 | 5/2005 |
| WO | WO2005051243 | 6/2005 |
| WO | WO2005074839 | 8/2005 |
| WO | WO2005104996 | 11/2005 |
| WO | WO2005117728 | 12/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006136760 | 12/2006 |
| WO | WO2007000654 | 1/2007 |
| WO | WO2006130460 A3 | 3/2007 |
| WO | WO2007034310 | 3/2007 |
| WO | WO2007063398 | 6/2007 |
| WO | WO2007078978 | 7/2007 |
| WO | WO2008099277 A3 | 8/2008 |
| WO | WO2008149223 | 12/2008 |
| WO | WO2009033100 | 3/2009 |
| WO | WO2011080535 | 7/2011 |

OTHER PUBLICATIONS

A Multicenter Retrospective Study of the Clinical Results of the Link SB Charite Intervertebral Prosthesis, S.L. Griffith, PhD, A.P. Shelokov, MD, K. Buttner-Janz, MD, Jean-Phillipe LeMaire, MD and W.S. Zeegers, MD, Spine, vol. 19, No. 16, pp. 1842-1849, Mar. 21, 1994.

A New Technique for the Three-Dimensional Study of the Spine in Vitro and In Vivo by Using a Motion-Analysis System, X. Liu, G. Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J.P. Kostuik, Spinal Fusion, vol. 29, No. 4, Oct. 1998, pp.

Centrode Patterns and Segmental Instability in Degenerative Disc Disease, S.D. Gertzban, MD, FRCSC, J. Seligman, MD, R. Holtby, MD, K.H. Chan, MD, A. Kapasourim BSc, M. Title, MD, BSc, (MED), FRCSC ©, and B. Cruickshank, MD, FRCPath, Spine, vol. 10, No. 3, pp. 257-261, Jan. 21, 1984.

Clinical Biomechanics of the Spine, A.A. White III, M.M. Panjabi, pp. 128-130, 2nd Edition, J.B. Lippincott Co., 1990.

Computer Analysis of Spinal Segment Motion in Degenerative Disc Disease with and Without Axial Loading, J.V. Seligman, S.D. Gertzbein, M. Title, A., Kapasouri, Spine, vol. 9., No. 6, pp. 566-573, Dec. 31, 1983.

FR 2 718 635 Preliminary Search Report, National Institute of Industrial Property (France), Jan. 16, 1995.

FR 2 730 159 Preliminary Search Report, National Institute of Industrial Property (France), Sep. 29, 1995.

FR 2 824 261 Preliminary Search Report, National Institute of Industrial Property (France), Feb. 25, 2002.

FR 2 831 796 Preliminary Search Report, National Institute of Industrial Property (France), Aug. 2, 2002.

FR 2 846 550 Preliminary Search Report, National Institute of Industrial Property (France), Jul. 10, 2003.

FR 2 865 629 Preliminary Search Report, National Institute of Industrial Property (France), Sep. 14, 2004.

FR 2 865 630 Preliminary Search Report, National Institute of Industrial Property (France), Jan. 12, 2005.

FR 2 869 528 Preliminary Search Report, National Institute of Industrial Property (France), Dec. 13, 2004.

Instantaneous Axis of Rotation as a Function of the Three Columns of the Spine, T.R. Haher, MD, M. O'Brien, MD, W.T. Felmly, MD, D. Welin, MD, G. Perrier, MD, J. Choueka, JD, V. Devlin, MD, A. Vassiliou, ME, and G. Chow, MD, Spine, vol. 17, No. 6, pp. S149-S154, Jan. 9, 1992.

Instantaneous Axis of Rotation of the Lumbar Intervertebral Joints, M.J. Pearcy, H. Bogduk, Spine, vol. 13, No. 9, pp. 1033-1041, Nov. 15, 1987.

Mobidisc (website) 1 page, www.Idrmedical.fr/mobidisc.htm, Sep. 19, 2004.

Motion Characteristics of the Normal Lumbar Spine in Young Adults: Instantaneous of Axis of Rotation and Vertebral Center Motion Analysis, t. Yoshioka, H. Tsuji, N.Hirano and S. Sainoh, Journal of Spinal Disorders, vol. 3, No. 2, pp. 103-113, 1990.
PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.
Relocation of the Bending Axis During Flexion-Extension of Lumbar intervertebral Disc and its Implications for Prolapse, J.A. Klein and D.W.L. Hukins, Spine, vol. 8, No. 6, pp. 659-664, Nov. 18, 1982.
The Effect of the Three Columns of the Spine on the Instantaneous Axis of Rotation in Flexion and Extension, T. R. Haher, M. Bergman, M. O'Brien, W.T. Felmly, J. Choueka, D. Welin, G. Chow, A. Vassiliou, Spine, vol. 16, No. 8, pp. S312-S318, Apr. 16, 1991.
USPTO OA of Feb. 6, 2007 in U.S. Appl. No. 11/109,276.
USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's Reply to USPTO OA of Feb. 13, 2009 in U.S. Appl. No. 11/109,276.
USPTO OA of Apr. 18, 2007 in U.S. Appl. No. 10/533,846.
Applicants' Response to USPTO OA of Apr. 18, 2007 in U.S. Appl. No. 10/533,846.
USPTO OA of Dec. 26, 2007 in U.S. Appl. No. 10/533,846.
Applicants' Response to USPTO OA of Dec. 26, 2007 in U.S. Appl. No. 10/533,846.
USPTO OA of Oct. 15, 2008 in U.S. Appl. No. 10/533,846.
Applicants' Response to USPTO OA of Oct. 15, 2008 in U.S. Appl. No. 10/533,846.
USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Apr. 13, 2009 in U.S. Appl. No. 11/341,007.
USPTO OA of Feb. 18, 2009 in U.S. Appl. No. 11/632,253.
Applicants' Response to USPTO OA of Feb. 18, 2009 in U.S. Appl. No. 11/632,253.
PCT/IB2008/000349 International Preliminary Report on Patentability PCT May 29, 2009.
PCT/IB2008/000349, Written Opinion of the International Search Authority PCT Aug. 16, 2009.
Progressive approach osteosynthesis device and preassembly method, U.S. Appl. No. 10/492,753, filed Aug. 9, 2004.
Implant for Osseous Anchoring with Polyaxial Head, U.S. Appl. No. 10/498,234, filed Dec. 7, 2004.
Osseous anchoring implant with a polyaxial head and method for installing the implant, U.S. Appl. No. 10/570,080, filed Jun. 9, 2006.
Device and method for sectioning a vertebral lamina, U.S. Appl. No. 10/575,065, filed Apr. 7, 2006.
Intervertebral Disc Prosthesis, U.S. Appl. No. 11/051,710, filed Feb. 4, 2005.
Intervertebral Disc Prosthesis and Instrumentation for Insertion of the Prosthesis Between the Vertebrae, U.S. Appl. No. 11/362,253, filed Feb. 24, 2006.
Transforanimal intersomatic cage for an intervertebral fusion graft and an instrument for implanting the cage, U.S. Appl. No. 11/378,165, filed Mar. 17, 2006.
Intervertebral disc prosthesis insertion assemblies, U.S. Appl. No. 11/676,237, filed Feb. 16, 2007.
Intersomatic cage with unified grafts, U.S. Appl. No. 11/767,386, filed Jun. 22, 2007.
Modular intervertebral prosthesis, U.S. Appl. No. 11/874,144, filed Oct. 17, 2007.
Vertebral Support Device, U.S. Appl. No. 11/958,285, filed Dec. 17, 2007.
Intervertebral disc prosthesis, surgical methods, and fitting tools, U.S. Appl. No. 12/025,677, filed Feb. 4, 2008.
Intersomatic cage, intervertebral prosthesis, anchoring device and implantation instruments, U.S. Appl. No. 12/134,884, filed Jun. 6, 2008.
Transverse spinal linking device and system, U.S. Appl. No. 12/172,074, filed Jul. 11, 2008.
Transforaminal intersomatic cage for an intervertebral fusion graft and an instrument for implanting the cage, U.S. Appl. No. 12/279,664, filed Apr. 22, 2009.
Intervertebral Disc Prosthesis, U.S. Appl. No. 12/360,050, filed Jan. 26, 2009.
Spinal Osteosynthesis Device and Preparation Method, U.S. Appl. No. 12/409,327, filed Mar. 23, 2009.
Intervertebral Disk Prosthesis, U.S. Appl. No. 12/424,364, filed Apr. 15, 2009.
Instrumentation and Methods for Inserting an Intervertebral Disc Prosthesis, U.S. Appl. No. 12/435,955, filed May 5, 2009.
Intervertebral disc prosthesis insertion assemblies, U.S. Appl. No. 12/527,373, filed Aug. 14, 2009.
Implant for Osseous Anchoring with Polyaxial Head, U.S. Appl. No. 12/562,704, filed Sep. 18, 2009.
Intervertebral Disc Prosthesis, U.S. Appl. No. 12/955,898, filed Nov. 29, 2010.
Instruments and Methods for Removing Fixation Devices from Intervertebral Implants, U.S. Appl. No. 13/158,761, filed Jun. 13, 2011.
Intervertebral Disc Prosthesis, U.S. Appl. No. 13/215,123, filed Aug. 22, 2011.
Interspinous Implant and Implantation Instrument, U.S. Appl. No. 13/369,650, filed Feb. 9, 2012.
Vertebral Cage Device With Modular Fixation, U.S. Appl. No. 13/438,352, filed Apr. 3, 2012.
Plate for osteosynthesis device and method of preassembling such device, U.S. Appl. No. 13/454,927, filed Apr. 24, 2012.
U.S. Patent & Trademark Office; Notice of Allowance in U.S. Appl. No. 10/476,565; Nov. 29, 2007; USPTO; Alexandria, Virgina; All Pages.
LDR Medical, by its attorneys; Amendment after Final in U.S. Appl. No. 10/476,565; Nov. 29, 2007; USPTO; Alexandria, Virgina; All Pages.
LDR Medical, by its attorneys; Reply to Office Action in U.S. Appl. No. 10/476,565; Nov. 6, 2007; USPTO; Alexandria, Virgina; All Pages.
U.S. Patent & Trademark Office; Office Action in U.S. Appl. No. 10/476,565; May 7, 2007; USPTO; Alexandria, Virgina; All Pages.
LDR Medical, by its attorneys; Reply to Office Action in U.S. Appl. No. 10/476,565; Jan. 18, 2007; USPTO; Alexandria, Virgina; All Pages.
U.S. Patent & Trademark Office; Office Action in U.S. Appl. No. 10/476,565; Jul. 18, 2006; USPTO; Alexandria, Virgina; All Pages.
LDR Medical, by its attorneys; Reply to Office Action in U.S. Appl. No. 12/025,677; Apr. 9, 2012; USPTO; Alexandria, Virgina; All Pages.
U.S. Patent & Trademark Office; Office Action in U.S. Appl. No. 12/025,677; Oct. 7, 2011; USPTO; Alexandria, Virgina; All Pages.
U.S. Patent & Trademark Office; Notice of Allowance in U.S. Appl. No. 10/533,846; Nov. 4, 2009; USPTO; Alexandria, Virgina; All Pages.
LDR Medical, by its attorneys; Reply to Office Action in U.S. Appl. No. 12/424,364; Feb. 27, 2012; USPTO; Alexandria, Virgina; All Pages.
U.S. Patent & Trademark Office; Office Action in U.S. Appl. No. 12/424,364; Jan. 26, 2012; USPTO; Alexandria, Virgina; All Pages.

LDR Medical, by its attorneys; Reply to Office Action in U.S. Appl. No. 12/424,364; Nov. 18, 2011; USPTO; Alexandria, Virgina; All Pages.
U.S. Patent & Trademark Office; Office Action in U.S. Appl. No. 12/424,364; May 18, 2011; USPTO; Alexandria, Virgina; All Pages.
U.S. Patent & Trademark Office; Office Action in U.S. Appl. No. 11/051,710; Dec. 15, 2011; USPTO; Alexandria, Virgina; All Pages.
LDR Medical, by its attorneys; Reply to Office Action in U.S. Appl. No. 11/051,710; Oct. 11, 2011; USPTO; Alexandria, Virgina; All Pages.
U.S. Patent & Trademark Office; Office Action in U.S. Appl. No. 11/051,710; Apr. 11, 2011; USPTO; Alexandria, Virgina; All Pages.
LDR Medical, by its attorneys; Reply to Office Action in U.S. Appl. No. 11/051,710; Jan. 20, 2011; USPTO; Alexandria, Virgina; All Pages.
U.S. Patent & Trademark Office; Office Action in U.S. Appl. No. 11/051,710; Jul. 20, 2010; USPTO; Alexandria, Virgina; All Pages.
LDR Medical, by its attorneys; Reply to Office Action in U.S. Appl. No. 11/051,710; Apr. 26, 2010; USPTO; Alexandria, Virgina; All Pages.
U. S . Patent & Trademark Office; Office Action in U.S. Appl. No. 11/051,710; Oct. 26, 2009; USPTO; Alexandria, Virgina; All Pages.
U.S. Patent & Trademark Office; Notice of Allowance in U.S. Appl. No. 11/098,266; Apr. 21, 2008; USPTO; Alexandria, Virgina; All Pages.
LDR Medical, by its attorneys; Reply to Office Action in U.S. Appl. No. 11/098,266; Feb. 6, 2008; USPTO; Alexandria, Virgina; All Pages.
U.S. Patent & Trademark Office; Office Action in U.S. Appl. No. 11/098,266; Aug. 6, 2007; USPTO; Alexandria, Virgina; All Pages.
LDR Medical, by its attorneys; Reply to Office Action in U.S. Appl. No. 11/098,266; May 23, 2007; USPTO; Alexandria, Virgina; All Pages.
U.S. Patent & Trademark Office; Office Action in U.S. Appl. No. 11/098,266; Nov. 29, 2006; USPTO; Alexandria, Virgina; All Pages.
LDR Medical, by its attorneys; Reply to Office Action in U.S. Appl. No. 11/098,266; Aug. 22, 2006; USPTO; Alexandria, Virgina; All Pages.
U.S. Patent & Trademark Office; Office Action in U.S. Appl. No. 11/098,266; Mar. 22, 2006; USPTO; Alexandria, Virgina; All Pages.
U.S. Patent & Trademark Office; Notice of Allowance in U.S. Appl. No. 12/391,086; Apr. 15, 2011; USPTO; Alexandria, Virgina; All Pages.
LDR Medical, by its attorneys; Reply to Office Action in U.S. Appl. No. 12/391,086; Jan. 31, 2011; USPTO; Alexandria, Virgina; All Pages.
U.S. Patent & Trademark Office; Office Action in U.S. Appl. No. 12/391,086; Jul. 29, 2010; USPTO; Alexandria, Virgina; All Pages.
U.S. Patent & Trademark Office; Notice of Allowance in U.S. Appl. No. 11/109,276; Dec. 8, 2009; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
LDR Medical, by its attorneys; Reply to Office Action in U.S. Appl. No. 12/360,050; Mar. 6, 2012; USPTO; Alexandria, Virgina; All Pages.
U.S. Patent & Trademark Office; Office Action in U.S. Appl. No. 12/360,050; Sep. 6, 2011; USPTO; Alexandria, Virgina; All Pages.
LDR Medical, by its attorneys; Reply to Office Action in U.S. Appl. No. 12/360,050; Jun. 16, 2011; USPTO; Alexandria, Virgina; All Pages.
U.S. Patent & Trademark Office; Office Action in U.S. Appl. No. 12/360,050; Dec. 17, 2010; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.
U.S. Patent & Trademark Office; Notice of Allowance in U.S. Appl. No. 11/180,868; Jul. 17, 2009; USPTO; Alexandria, Virgina; All Pages.
LDR Medical, by its attorneys; Reply to Office Action in U.S. Appl. No. 12/435,955; Apr. 11, 2012; USPTO; Alexandria, Virgina; All Pages.
U.S. Patent & Trademark Office; Office Action in U.S. Appl. No. 12/435,955; Oct. 11, 2011; USPTO; Alexandria, Virgina; All Pages.
U.S. Patent & Trademark Office; Notice of Allowance in U.S. Appl. No. 11/341,007; Jul. 26, 2010; USPTO; Alexandria, Virgina; All Pages.
LDR Medical, by its attorneys; Reply to Office Action in U.S. Appl. No. 11/341,007; Jun. 17, 2010; USPTO; Alexandria, Virgina; All Pages.
U.S. Patent & Trademark Office; Office Action in U.S. Appl. No. 11/341,007; Dec. 17, 2009; USPTO; Alexandria, Virgina; All Pages.
LDR Medical, by its attorneys; Reply to Office Action in U.S. Appl. No. 11/341,007; Oct. 13, 2009; USPTO; Alexandria, Virgina; All Pages.
LDR Medical, by its attorneys; Reply to Office Action in U.S. Appl. No. 12/955,898; Apr. 19, 2012; USPTO; Alexandria, Virgina; All Pages.
U.S. Patent & Trademark Office; Office Action in U.S. Appl. No. 12/955,898; Mar. 19, 2012; USPTO; Alexandria, Virgina; All Pages.
LDR Medical, by its attorneys; Appeal Brief in U.S. Appl. No. 11/362,253; Apr. 9, 2012; USPTO; Alexandria, Virgina; All Pages.
U.S. Patent & Trademark Office; Office Action in U.S. Appl. No. 11/362,253; Mar. 8, 2011; USPTO; Alexandria, Virgina; All Pages.
LDR Medical, by its attorneys; Reply to Office Action in U.S. Appl. No. 11/362,253; Dec. 20, 2010; USPTO; Alexandria, Virgina; All Pages.
U.S. Patent & Trademark Office; Office Action in U.S. Appl. No. 11/362,253; Jun. 18, 2010; USPTO; Alexandria, Virgina; All Pages.
LDR Medical, by its attorneys; Reply to Office Action in U.S. Appl. No. 11/362,253; Apr. 15, 2010; USPTO; Alexandria, Virgina; All Pages.
U.S. Patent & Trademark Office; Office Action in U.S. Appl. No. 11/362,253; Oct. 15, 2009; USPTO; Alexandria, Virgina; All Pages.
LDR Medical, by its attorneys; Reply to Office Action in U.S. Appl. No. 11/362,253; Aug. 18, 2009; USPTO; Alexandria, Virgina; All Pages.
U.S. Patent & Trademark Office; Office Action in U.S. Appl. No. 11/362,253; Feb. 18, 2009; USPTO; Alexandria, Virgina; All Pages.
U.S. Patent & Trademark Office; Notice of Allowance in U.S. Appl. No. 10/494,418; Sep. 20, 2005; USPTO; Alexandria, Virgina; All Pages.
U.S. Patent & Trademark Office; Office Action in U.S. Appl. No. 12/134,884; Jan. 31, 2012; USPTO; Alexandria, Virgina; All Pages.
U.S. Patent & Trademark Office; Office Action in U.S. Appl. No. 12/527,373; Dec. 21, 2011; USPTO; Alexandria, Virgina; All Pages.
U.S. Patent & Trademark Office; Office Action in U.S. Appl. No. 12/025,677; Jun. 29, 2012; USPTO; Alexandria, Virgina; All Pages.
LDR Medical, by its attorneys; Interview Summary and Terminal Disclaimer in U.S. Appl. No. 12/424,364; May 22, 2012; USPTO; Alexandria, Virgina; All Pages.
U.S. Patent & Trademark Office; Notice of Allowance in U.S. Appl. No. 12/424,364; Jul. 24, 2012; USPTO; Alexandria, Virgina; All Pages.
U.S. Patent & Trademark Office; Office Action in U.S. Appl. No. 12/424,364; May 23, 2012; USPTO; Alexandria, Virgina; All Pages.
LDR Medical, by its attorneys; Reply to Office Action in U.S. Appl. No. 12/424,364; Jul. 6, 2012; USPTO; Alexandria, Virgina; All Pages.
U.S. Patent & Trademark Office; Notice of Allowance in U.S. Appl. No. 12/360,050; Jul. 6, 2012; USPTO; Alexandria, Virgina; All Pages.
U.S. Patent & Trademark Office; Office Action in U.S. Appl. No. 12/955,898; Jun. 1, 2012; USPTO; Alexandria, Virgina; All Pages.
U.S. Patent & Trademark Office; Examiner's Answer to Appeal Brief in U.S. Appl. No. 11/362,253; Jun. 20, 2012; USPTO; Alexandria, Virgina; All Pages.
LDR Medical, by its attorneys; Reply to Office Action in U.S. Appl. No. 12/527,373; Jun. 21, 2012; USPTO; Alexandria, Virgina; All Pages.
World Intellectual Property Organization; International Preliminary Report on Patentability for PCT Pub'n No. WO2005074839; Jan. 16, 2006; WIPO; Geneva, Switzerland; all pages.

World Intellectual Property Organization; International Preliminary Report on Patentability for PCT Pub'n No. WO2005104996; Jun. 28, 2006; WIPO; Geneva, Switzerland; all pages.
World Intellectual Property Organization; International Preliminary Report on Patentability for PCT Pub'n No. WO2006120505; Feb. 22, 2007; WIPO; Geneva, Switzerland; all pages.
World Intellectual Property Organization; International Preliminary Report on Patentability for PCT Pub'n No. WO2007000654; Jul. 19, 2007; WIPO; Geneva, Switzerland; all pages.
World Intellectual Property Organization; International Preliminary Report on Patentability for PCT Pub'n No. WO2007034310; Aug. 14, 2007; WIPO; Geneva, Switzerland; all pages.
World Intellectual Property Organization; International Preliminary Report on Patentability for PCT Pub'n No. WO2007063398; Nov. 12, 2007; WIPO; Geneva, Switzerland; all pages.
World Intellectual Property Organization; International Preliminary Report on Patentability for PCT Pub'n No. WO2008149223; Aug. 5, 2009; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; International Search Report for PCT Pub'n No. WO2007000654; Mar. 14, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; International Search Report for PCT Pub'n No. WO2008099277; Nov. 7, 2008; WIPO; Geneva, Switzerland; all pages.
World Intellectual Property Organization; International Search Report for PCT Pub'n No. WO2008149223; Oct. 31, 2008; WIPO; Geneva, Switzerland; all pages.
World Intellectual Property Organization; International Search Report for PCT Pub'n No. WO2011080535; Jan. 24, 2011; WIPO; Geneva, Switzerland; all pages.
World Intellectual Property Organization; Written Opinon of the International Searching Authority for PCT Pub'n No. WO2005074839; Jun. 24, 2005; WIPO; Geneva, Switzerland; all pages.
World Intellectual Property Organization; Written Opinon of the International Searching Authority for PCT Pub'n No. WO2005104996; Sep. 12, 2005; WIPO; Geneva, Switzerland; all pages.
World Intellectual Property Organization; Written Opinon of the International Searching Authority for PCT Pub'n No. WO2006120505; Aug. 21, 2006; WIPO; Geneva, Switzerland; all pages.
World Intellectual Property Organization; Written Opinon of the International Searching Authority for PCT Pub'n No. WO2007000654; Mar. 14, 2007; WIPO; Geneva, Switzerland; all pages.
World Intellectual Property Organization; Written Opinon of the International Searching Authority for PCT Pub'n No. WO2007034310; Feb. 13, 2007; WIPO; Geneva, Switzerland; all pages.
World Intellectual Property Organization; Written Opinon of the International Searching Authority for PCT Pub'n No. WO2007063398; Jul. 13, 2007; WIPO; Geneva, Switzerland; all pages.
World Intellectual Property Organization; Written Opinon of the International Searching Authority for PCT Pub'n No. WO2008099277; Nov. 7, 2008; WIPO; Geneva, Switzerland; all pages.
World Intellectual Property Organization; Written Opinon of the International Searching Authority for PCT Pub'n No. WO2008149223; Oct. 31, 2008; WIPO; Geneva, Switzerland; all pages.
National Institute of Industrial Property (France); Preliminary Search Report in Fench Pub. No. FR2879436; Aug. 11, 2005; National Institute of Industrial Property (France); France; all pages.
National Institute of Industrial Property (France); Preliminary Search Report in Fench Pub. No. FR2887762; Dec. 21, 2005; National Institute of Industrial Property (France); France; all pages.
National Institute of Industrial Property (France); Preliminary Search Report in Fench Pub. No. FR2891135; Jun. 27, 2006; National Institute of Industrial Property (France); France; all pages.
National Institute of Industrial Property (France); Preliminary Search Report in Fench Pub. No. FR2893838; Aug. 4, 2006; National Institute of Industrial Property (France); France; all pages.
National Institute of Industrial Property (France); Preliminary Search Report in Fench Pub. No. FR2916956; Jan. 30, 2008; National Institute of Industrial Property (France); France; all pages.

* cited by examiner

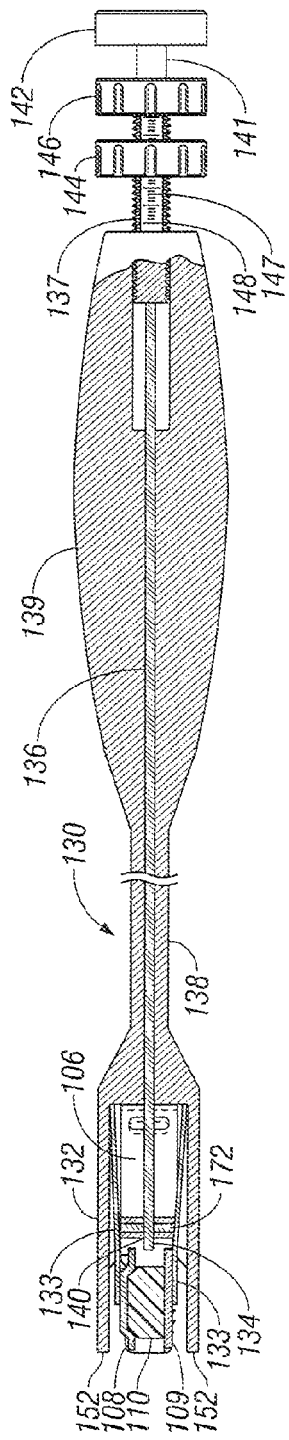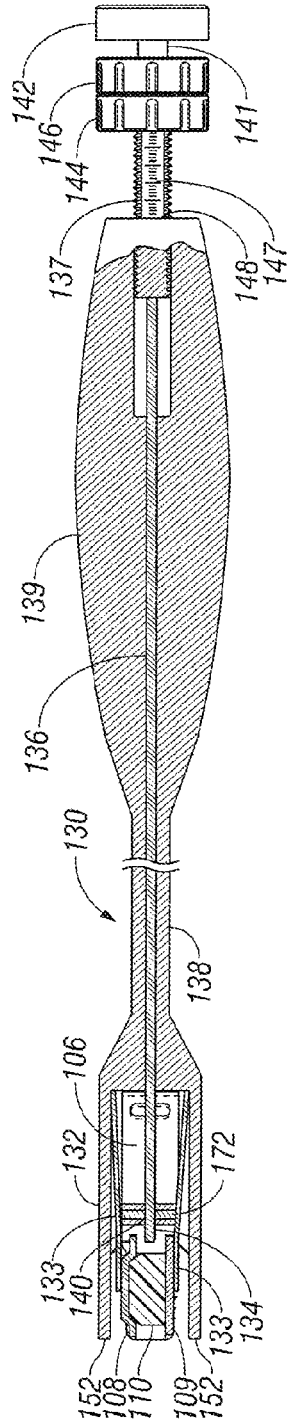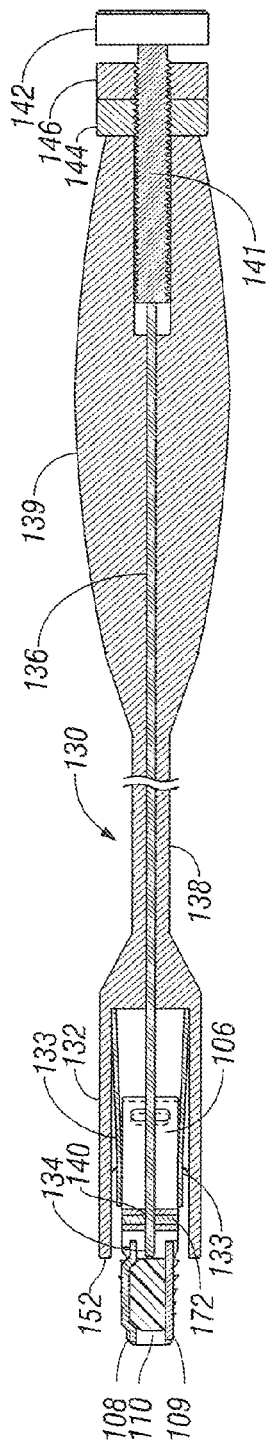

INTERVERTEBRAL DISC PROSTHESIS INSERTION ASSEMBLIES

TECHNICAL FIELD

This disclosure relates to intervertebral disc prostheses for replacement of natural intervertebral discs.

BACKGROUND

A healthy intervertebral disc is flexible enough to allow movement between adjacent vertebrae or between a vertebra and another adjacent spinal column element, such as the coccyx (the most inferior portion of the vertebral column, resulting from the fusion of the four coccygeal vertebrae) and the sacrum (a triangular bone that is the posterior skeletal element forming the pelvis, formed by 5 fused vertebrae). This movement accommodates bending of the spine. Disease or degeneration of the tissues of a natural intervertebral disc often leads to intense pain and reduced mobility. When degeneration or disease of the natural intervertebral disc has progressed to the point where non-operative care such as medication, injections, and/or physical therapy is ineffective, surgical intervention may be required.

A common procedure for treatment of degenerative or diseased intervertebral discs involves removal of the natural tissues of the disc and fusion of the adjacent vertebrae. Fusion eliminates the mobility between the adjacent vertebrae, however, and can transfer stresses and movements to the intervertebral discs above and/or below the point of fusion.

Intervertebral disc prostheses have been developed to mitigate some of the problems caused by intervertebral fusion. In particular, various designs of intervertebral disc prostheses can provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from postoperative immobilization instrumentation typically present in fusion procedures.

U.S. patent application Ser. Nos. 10/476,565, 10/533,846, 11/051,710, and 11/362,253, each of which is assigned to the assignee of the present application and each of which is incorporated herein by reference for all purposes, disclose various intervertebral disc prosthesis configurations. In many of these configurations, the prosthesis may have an upper plate supporting the upper vertebra, a lower plate supporting the lower vertebra, and a mobile core or nucleus that provides some range of articulation between the upper plate and the lower plate.

Prior to the surgical implantation procedure, measurements often are made of the plates of the upper and lower vertebrae to confirm the viability of the procedure. Following discectomy in various representative procedures, the depth and width of the intervertebral space are measured, and a determination is made of an appropriate vertical spacing of the adjacent vertebra and the sizes of the upper and lower disc prosthesis plates and the core.

Typically, there are several selections for the depth and width of the intervertebral prosthesis plates and for the height of the core, depending on the type of intervertebral disc prosthesis. For example, the LDR Medical Mobi-C™ cervical disc prosthesis currently can be configured with any of 4 plate sizes and 3 core heights, and the LDR Medical Mobidisc™ lumbar disc prosthesis currently can be configured with any of 18 plate sizes and 6 core heights. In addition, the surgeon may wish to accommodate or correct a lordosis or kyphosis by using one or more plates having an angular offset between the vertebral axis implied by a normal to the plate's vertebral contact surface and a mean, or neutral, normal axis implied by the plate's core contact surface. Thus, even within a single product line, there may be numerous combinations of individual disc prosthesis elements available to suit the requirements of a particular patient.

In various intervertebral prosthesis product systems, the upper plates, the lower plates, and the cores are provided to the sterile field of the surgical suite individually. Once the proper configuration of the upper plate, the lower plate, and the core has been determined, typically the surgical staff must acquire the proper upper plate, lower plate, and core from inventory.

The components of the prosthesis typically are then assembled for mounting with or loading into a prosthesis insertion tool, or assembled directly with the insertion tool. In some systems, an assembly stand or jig is used for assembling the prosthesis components and loading the assembled prosthesis into an insertion tool. The selection and assembly process can be time consuming and awkward, potentially resulting in delays during the surgical proceeding. Handling of the components during assembly process can compromise the sterility of the prosthesis, and the use of additional handling equipment, such as an assembly stand or jig, can require further sterilization procedures, increase the complexity of the procedure, and clutter the surgical suite.

In some systems, an assortment of insertion tools are each configured for use with a single size or a limited range of sizes of the various prosthesis component combinations. Generally, the required size and configuration of the various prosthesis components will not be known until the surgical procedure has commenced. Thus, the surgeon will have to select the proper insertion tool during the procedure, following the determination of the proper sizes and configurations of the various prostheses components. The surgical staff therefore must disinfect and sterilize several insertion tools to have a full selection of the insertion tools at hand during the procedure. During the procedure, selection of the appropriate tool and confirmation of the selection will add to the duration and complexity of the surgical procedure. In various designs of insertion tools, however, the operative components of the insertion tool body are the same regardless of the prosthesis configuration, and only the tool's insertion adapter (for example, a head, holder, or other carrier of the assembled prosthesis) differs among the various insertion tools. Often, the differences among the various insertion adapters are dictated solely by the differences in sizes and configurations of the prosthesis components.

SUMMARY

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various embodiments, the prosthesis and an insertion tool are provided in a sterile pack, with the prosthesis components and the insertion holder sterilized and packaged in one or more types or layers of sterile packaging. Intervertebral disc prosthesis insertion assemblies, intervertebral disc prosthesis insertion systems, intervertebral disc prosthesis delivery and insertion systems, methods of inserting an intervertebral disc prosthesis between adjacent elements of a spinal column, methods of inserting an intervertebral disc prosthesis between adjacent elements of a spinal column, and methods of aseptically delivering an intervertebral disc prosthesis insertion assembly to a sterile field are also disclosed.

BRIEF DESCRIPTION OF THE SEVERAL VIEWS OF THE DRAWINGS

FIGS. 6A, 6B, and 6C depict various views of an insertion tool body.

DETAILED DESCRIPTION OF VARIOUS EMBODIMENTS

Figure 1:
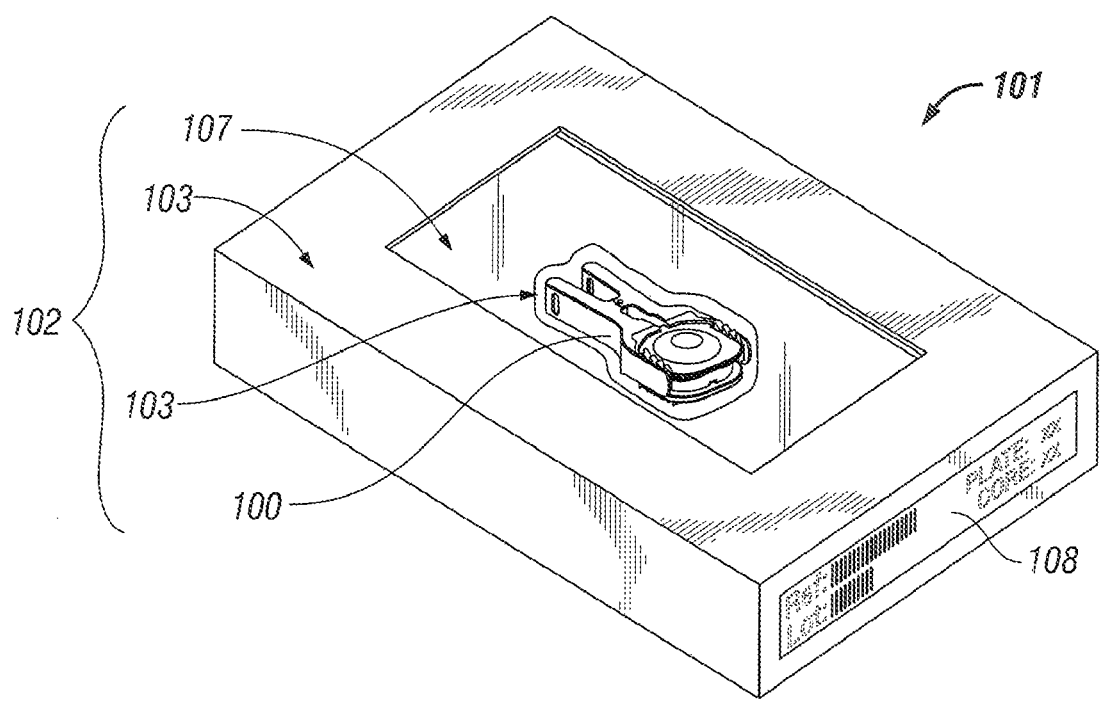
FIG. 1 depicts a sterile pack comprising a prosthesis insertion assembly.
Figure 2:
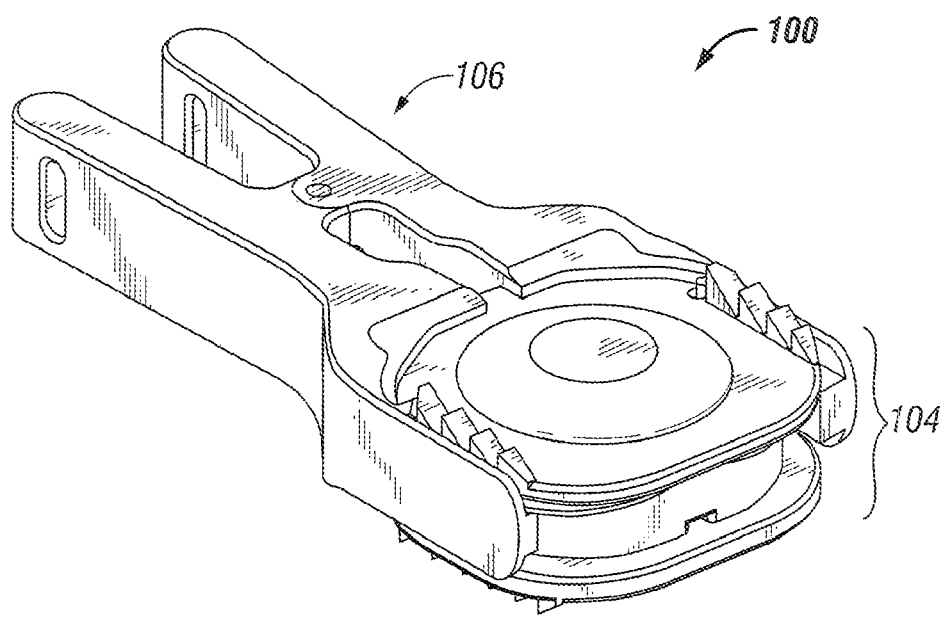
FIG. 2 depicts a prosthesis insertion assembly.

FIG. 1 depicts one of many possible embodiment of a packaged intervertebral disc prosthesis insertion assembly (101). In this embodiment, a sterile insertion adapter (106) and sterile components of an intervertebral disc prosthesis (104) may be assembled together to form a sterile prosthesis insertion assembly (100) as shown in FIG. 2, which is disposed in primary, or inner, sterile packaging (103) and in secondary, or outer, sterile packaging (103) to form a sterile pack (102). The components of the intervertebral disc prosthesis (104) may be assembled with the insertion adapter (106) and provided to the sterile field of a surgical suite pre-configured and ready to use.

FIG. 2 depicts one of many potential embodiments of ant insertion assembly (100). Various embodiments of the insertion assembly (100) may comprise an intervertebral disc prosthesis (104) of the type manufactured by LDR Medical, Inc., and an insertion adapter (106), which holds the prosthesis (104) and couples with, mounts to or otherwise joins or engages a detachable or demountable surgical tool body (130), for example as illustrated in FIG. 4, used in implanting the prosthesis (104). In this embodiment, a clip (126), for example as illustrated in FIG. 3, provides additional restraint to the components of prosthesis (104).

Figure 3:
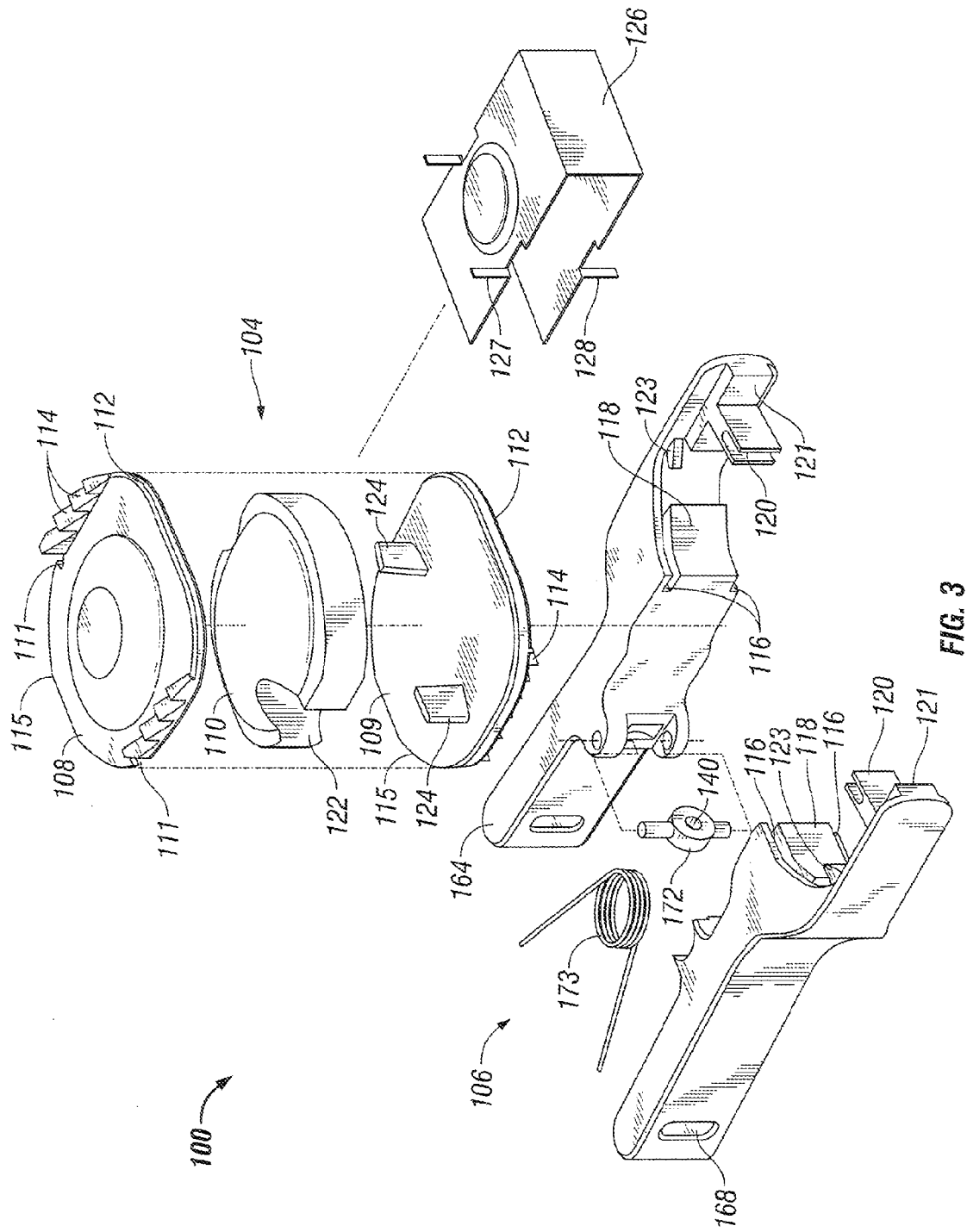
FIG. 3 depicts details of a prosthesis insertion assembly.
Figure 4:
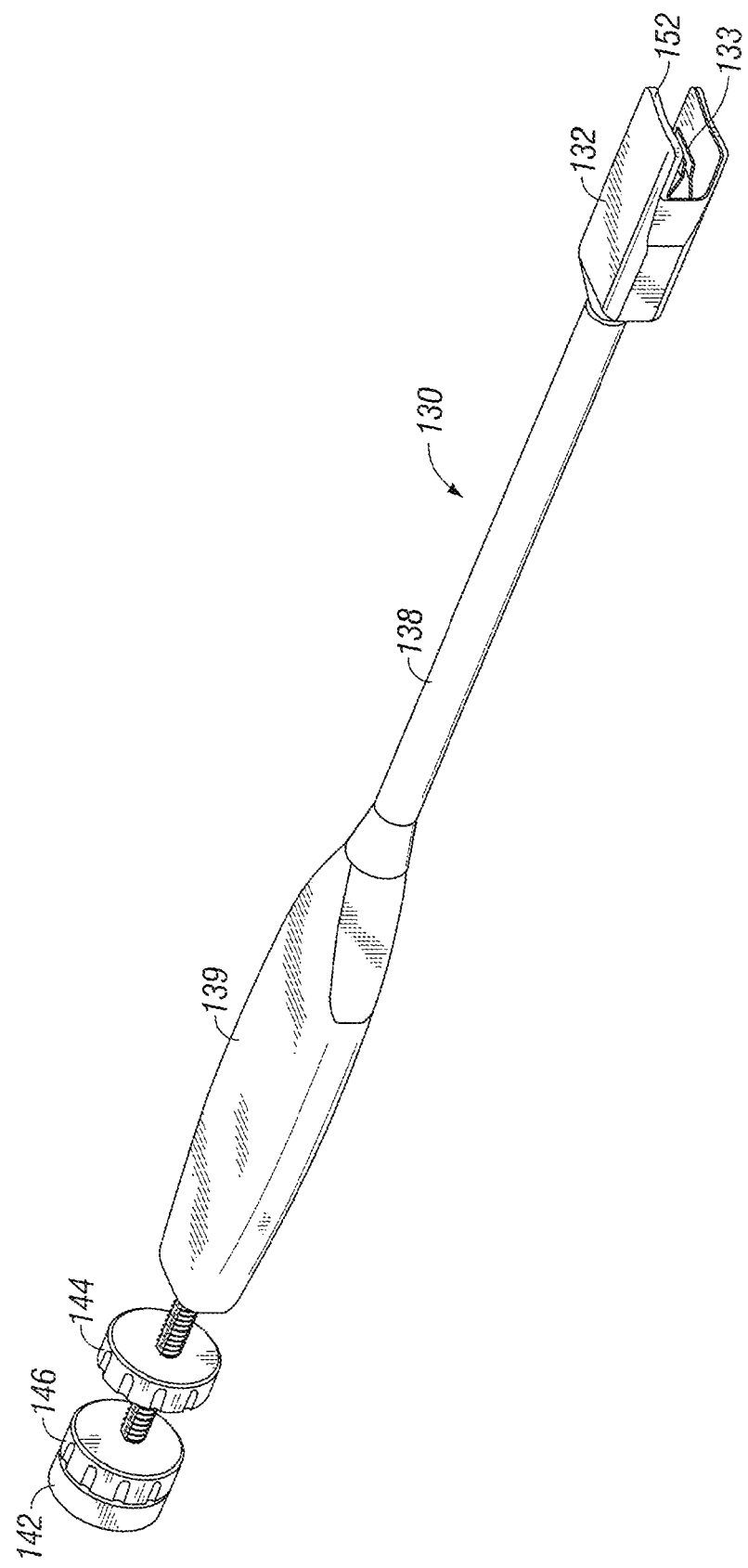
FIG. 4 depicts an insertion tool body.

FIG. 3 shows an exploded view of an embodiment of a prosthesis (104) and an insertion adapter (106). The prosthesis (104) in this embodiment comprises a first plate, such as upper plate (108), a second plate, such as lower plate (109), and a mobile core (110). The configurations of "upper" and "lower" plates generally are reversible, and the designation of the plates as "first" and "second," of course, is purely arbitrary. The upper and lower plates (108, 109) preferably may be made of chromium, cobalt, and molybdenum, but other compositions may used. In various preferred embodiments, the core may be made of an ultrahigh molecular weight polyethylene. A titanium and hydroxyapatite plasma spray coating may optionally be applied to the vertebral contact surfaces of the upper and lower plates (108, 109) to encourage at least partial fusion with the adjacent vertebrae by bony ingrowth or other forms of adhesion.

The prosthesis (104) in various embodiments may contain other features. For example, second plate (109) may be configured with core-travel stops, for example posts (124) as illustrated, that limit the translational and rotational movement of core (110). In such embodiments, contact between the stops (124) and the recesses (122) along the perimeter of the core body may be configured to limit the translational and rotational movement of the core (110). The plates (108, 109) optionally may have angled edges (115) configured for complementary contact with optional angled contact surfaces (116) of the insertion adapter (106), the benefits of which are described in greater detail below.

Additional optional features of the prosthesis (104) may facilitate implantation of the prosthesis and its stability once implanted. For example, one or more of the edges of the prosthesis (104) that encounter the surfaces of the vertebrae (150) during prosthesis insertion may be beveled, for example edges (112) of the upper plate (108) and the lower plate (109), which may reduce the effort required to insert the prosthesis (104). Alternate embodiments may not contain this bevel at all, or may be beveled in only a few strategic locations around the perimeter of the plates (108, 109). Various embodiments also may have anchors (114) that, for example, may comprise notches or teeth disposed on either or both of the plates (108, 109) in the region of one or more edges of the prosthesis (104), or one or more anchors may be elsewhere along either or both of the vertebral contact surfaces of the plates (108, 109). The anchors (114) may be configured in such a way that they minimize the force required during the implantation of the prosthesis (104), while opposing subsequent movement of the prosthesis. After the prosthesis (104) is implanted, anchors (114) preferably stabilize the prosthesis (104) and oppose movement relative to the vertebrae (150) in multiple ways. For example, the anchors (114) may provide teeth opposing movement, primarily in the direction of removal, between the prosthesis (104) and the vertebrae (150), thus helping to keep the prosthesis (104) in place after implantation and during withdrawal of the insertion adapter (106). The surfaces of the plates (108, 109) also may have a porous biocompatible coating, for example as described above, that also allows adhesion of the osseous tissue and its fusion with the prosthesis. Once osseous tissue has adhered to the plates (108, 109) and grown around the anchors (114), a strong connection may be formed between each of the plates (108, 109) of the prosthesis (104) and the respective adjacent vertebra (150). In alternate embodiments, the porous, biocompatible coating may be replaced or supplemented with a porous, bioactive coating, which may stimulate the formation of osseous tissue, and/or with an antiseptic coating, which may deter or counteract infection at the surface of the implant.

After discectomy (whether complete or partial) and distraction of adjacent elements of a spinal column such as vertebrae (150), prosthesis implantation surgical procedures may involve measurements of intervertebral disc space. These measurements may be used to determine the dimensions and configurations of the upper plate (108), the lower plate (109), and the mobile core (110) to be implanted. In various embodiments, the prosthesis (104) generally may be configured to assist in the correction of various types of spinal disorders, including lordosis and kyphosis. Correction of lordosis or kyphosis may involve imposition of an angle, for example between 0 and 15 degrees, between the upper plate (108) and the lower plate (109) in the postero-anterior direction. The upper plate (108), the lower plate (109), or the core (110) may be configured to assist in imposing such an angle, for example as discussed in U.S. patent application Ser. No. 10/476,565 assigned to the assignee of the present application. In addition, the plates (108, 109) and the core (110) generally have dimensions and configurations selected for the particular patient in which the prosthesis (104) will be implanted. Often, in practice the dimensions and configurations of the prosthesis (104) will not be known until well into the surgical procedure. Accordingly, for any particular patient the surgical staff will need an assortment of prosthesis insertion assembly configurations on hand.

In various embodiments, the plates (108, 109) and core (110) of the prosthesis (104) may be retained by or releasably mounted to an insertion adapter (106). The insertion adapter (106) may be configured in many ways, such as a head, holder, or other carrier of an assembled prosthesis (104), for example. The insertion adapter (106) optionally may have jaws (121) that hold the prosthesis by grasping or pinching the lateral edges of the upper and lower plates of the prosthesis. The insertion adapter (106) may further comprise one or more optional retainers, such as mounting dogs (120). The dogs (120) may engage a respective recess (122) located in the mobile core (110) and contact or grasp a respective one of the posts (124) located on the lower plate (109). The dogs (120) may have surfaces configured to substantially match the spacing and/or configuration of the faces of the recesses (122). One or more of the dogs (120) may be equipped with a channel substantially matching the edge of one of the respective posts (124), to increase the effectiveness of the grasp on the lower plate (109). In addition, the insertion adapter (106) nay optionally have additional retaining, grasping, or securing means, for example the illustrated latches (123) disposed on jaws (121), which may engage complementary retaining, grasping, or securing means, such as a receiver, recess, notch, etc., for example the recesses (111) disposed along opposite lateral edges of plate (108).

The insertion adapter (106) in various embodiments also may comprise angled contact surfaces (116) configured for complementary contact with optional angled edges (115) of the prosthesis plates (108, 109). An optional shoulder (118) may be configured for complementary contact with the perimeter of the core (110). The combined height of the contact surfaces (116) and the shoulder (118) may preferably be substantially equal to the distance between the plates (108, 109) of an assembled prosthesis (104). The contact surfaces (116) and the shoulder (118) in various embodiments thus may combine to provide a surface of the insertion adapter (106) complementary to, and substantially fitting, the prosthesis (104) when assembled with, or mounted or attached to, the insertion adapter (106). A complementary fit between angled structures such as this may help stabilize the prosthesis (104) and push its components uniformly into the intervertebral disc space, preventing unwanted rotation or transverse movements of the prosthesis (104) or its components during insertion.

Various embodiments may incorporate any or all of the structures discussed above, but may also have other attachment and support mechanisms. For example, some embodiments optionally may have additional mount points, such as in the upper plate (108), the lower plate (109), or both. Other alternative embodiments could have retainers such as pins or clips that fit into one or more cavities or recesses of various prosthesis components, or one or more of many other methods that could be used to grasp objects and allow for convenient release when desired.

The insertion adapter (106) in various embodiments may have actuator means for releasing the intervertebral this prosthesis (104). In various embodiments, the actuator may be configured as spring-loaded arms, tangs, shanks, or other actuating means (164) articulable about articulating means such as a hinge pin (172). Alternatively, the insertion adapter (106) may have an integral hinge portion about which the arms, tangs, shanks, or other actuating means (164) articulate, for example comprising a flexible material such as plastic or rubber or stress/strain relief features such as cuts or voids. Those of skill in the art, following appreciation of this disclosure, will recognize that many other structural configurations nay be devised for the insertion adapter (106) to grasp the intervertebral disc prosthesis (104) and release the intervertebral this prosthesis (104) when inserted in an intervertebral disc space.

Some embodiments of the prosthesis insertion assembly (100) optionally may have a clip (126) that wraps around the assembled prosthesis (104) and holds the plates (108, 109) to the core (110). Retaining means such as the clip (126) augment the insertion adapter (106) in maintaining assembly of the prosthesis (104) during transport and/or during mounting, attaching, or assembling the insertion adapter (106) to or with the insertion tool body (130). Optionally, clip (126) may have one or more removal means to facilitate removal of the clip when the prosthesis insertion assembly (100) is assembled with, or mounted or attached to, an insertion tool body (130), such as tabs (127, 128) on its upper and lower surfaces, respectively, as discussed further below.

In some preferred embodiments, the components of the intervertebral disc prosthesis (104) and the insertion adapter (106) may be sterilized using gamma radiation. Following sterilization, the components may be packaged in primary sterile packaging (103) to form a sterile pack (102), preferably with the components of the intervertebral disc prosthesis (104) and the insertion adapter (106) assembled as an insertion assembly (100), although packaging disassembled components of the intervertebral disc prosthesis (104) and the insertion adapter (106) is within the scope of this invention. In various preferred embodiments, the components of the intervertebral disc prosthesis (104) and the insertion adapter (106) that are packaged in primary sterile packaging (103), whether assembled or disassembled, may be further packaged in a box or other container and enclosed in secondary sterile packaging (103) to form a sterile pack (102). The sterile packaging (103) may comprise bubble packaging, blister packaging, shrink wrapping, or other packaging configuration known to be suitable for maintaining the sterility of a medical implant. Sterile packaging (103) in some embodiments preferably may have an oxygen absorbing packet, for example to reduce the potential for oxidative degradation of a polyethylene core (110) or other components. In preferred embodiments, the sterile pack (102) preferably may be made ready for delivery or transport to a sterile field of a surgical suite, directly or through a distributor.

Sterile packs (102) of insertion assemblies (100) preferably bear identifying information. For example, various embodiments optionally have a package label with identifying information (180). The identifying information may include a use-before-date, the lot number and reference or serial number for the insertion assembly (100) or its components, a sterilization control label, and/or size and configuration information for the plates (108, 109) and the core (110). Preferably, the packaging label allows complete traceability of insertion assembly (100) from initial manufacturing through final implantation and service in a particular patient.

Various embodiments described herein provide a surgical staff with an assortment or other inventory of pre-sterilized, pre-configured, and pre-assembled insertion assemblies (100). Optionally, a packaged intervertebral disc prosthesis insertion assembly may be provided with the intervertebral disc prosthesis (104) disassembled, along with an insertion adapter (106) preconfigured for use with the intervertebral disc prosthesis (104) following its assembly. In such embodiments, the components of the intervertebral disc prosthesis (104) typically would be assembled with the insertion adapter (106) in the sterile field to form an insertion assembly (100).

During a surgical procedure in various embodiments, the surgeon determines the appropriate dimensions and configurations of prosthesis (104). Measurements of the intervertebral disc space may, for example, be used in such a determination. Preferably, the surgical team may obtain the appropriate prosthesis insertion assembly (100) within the sterile field of the surgical suite from an inventory of prosthesis insertion assemblies (100).

In various disclosed embodiments such as shown in FIG. 4, whether providing the intervertebral disc prosthesis (104) assembled or disassembled, the prosthesis insertion assembly (100) may be configured for use with a detachable or demountable tool body (130), which may be used during the surgical procedure to implant the prosthesis (104) in the intervertebral disc space. The prosthesis insertion assembly (100) and the insertion tool body (130) preferably may be arranged or assembled for use, for example by attaching or mounting the prosthesis insertion assembly (100) to an insertion tool body (130), within the sterile field of a surgical suite.

Figure 5A:
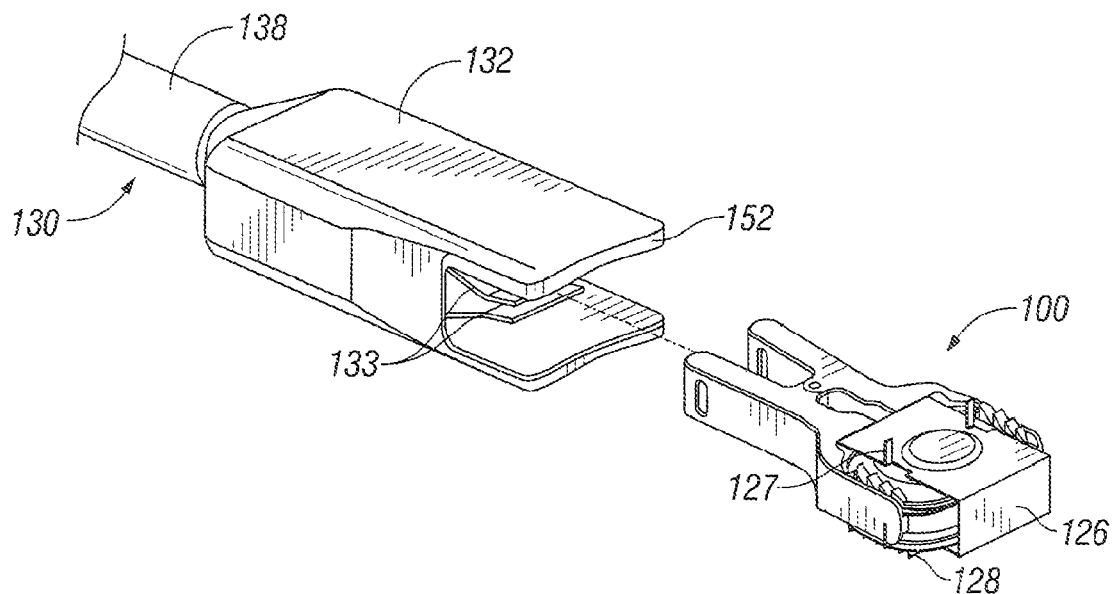
FIGS. 5A and 5b depict components of an insertion tool body and a prosthesis insertion assembly.
Figure 5B:
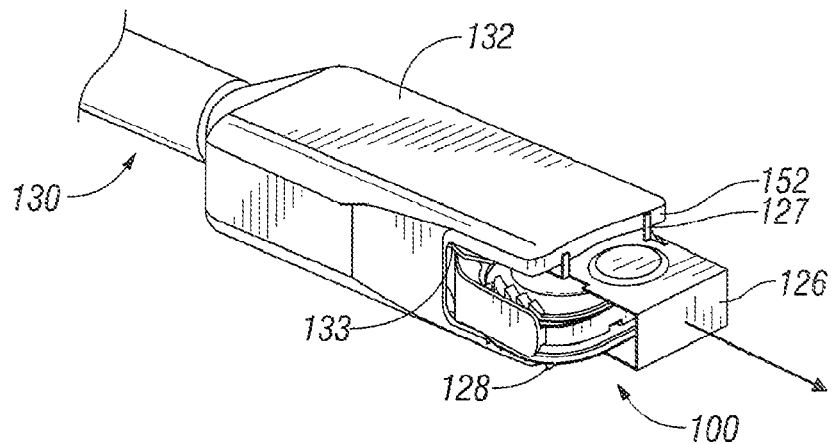

After removal from the sterile pack (102), the insertion assembly (100) and a detachable or demountable insertion tool body (130) are assembled. For the embodiments shown in FIGS. 5A and 5B, the prosthesis insertion assembly (100) may be lined up with a support (132), such as the illustrated housing for example, arranged to receive and support the prosthesis insertion assembly (100) during the implantation procedure. Preferably the insertion tool body (130) may be adapted for use with all, or at least a wide assortment, of the various dimensions and configurations of intervertebral disc prostheses (104) available. There may be a wide variance in the heights of the various prostheses (104) in some embodiments of intervertebral disc prosthesis delivery and insertion systems. The support (132) optionally may be equipped with one or more retainers, for example the tongues (133) illustrated, to retain the prosthesis components in assembly. Other embodiments that deploy such retainers may use structures such as clips, pawls, springs, or other biasing components. Retainers such as tongues (133) may help center and support a wide variety of prosthesis dimensions and configurations with respect to support (132).

After appreciating the present disclosure, those of skill in the art will readily recognize numerous alternative means of mounting, coupling, assembling, attaching, or otherwise engaging a prosthesis insertion assembly (100) and an insertion tool body (130). For example, the insertion tool body (130) may be equipped with an actuator (136), such as a rod, shaft, cable, or other transmission or control structure, for example as illustrated in FIGS. 6A, 6B, and 6C. The actuator (136) in various embodiments may have engagement means, for example the illustrated threaded end (134) of the rod (136), to engage or connect with a coupler (140), for example the threaded hole illustrated in FIG. 3, of the insertion adapter (106). Once so engaged, the rod (136) may hold and push the insertion adapter (106) during the implantation procedure.

The prosthesis insertion assembly (100) optionally may be attached or mounted to the insertion tool body (130) by engagement of the threaded end (134) with threaded hole (140). The insertion assembly (100) may be disposed by hand at least partially within support (132), at least to the point where the insertion assembly (100) engages the threaded end (134). The insertion assembly (100) may be further disposed by hand fully within support (132), causing the threaded end (134) to recess into the member (138) of the insertion tool body (130). At this point, the threaded end (134) may be rotated in threaded hole (140) until appropriate engagement of the threads is achieved and the prosthesis insertion assembly (100) is firmly retained in support (132). Alternatively, the threaded end (134) may, upon initial engagement with threaded hole (140), be rotated in threaded hole (140) until the prosthesis insertion assembly (100) is drawn fully within and retained in support (132). Regardless of how the prosthesis insertion assembly (100) is disposed into support (132), tabs (127, 128) on the respective upper and lower surfaces clip (126) may be configured to contact leading edges (152) of support (132), respectively, well before the insertion assembly (100) is seated in the insertion assembly (100), causing the clip (126) to detach from the prosthesis (104) as the insertion assembly (100) is further moved into support (132), for example as depicted in FIG. 5.

As shown in FIGS. 6A, 6B, and 6C, for some embodiments the actuator (136) may transit the member (138), which for example may be configured as a frame or shaft as illustrated. The actuator (136) may be equipped with a control at the end the insertion tool body (130) opposite the support (132), such as the knob (142) or a lever, button, or other control structure. In various embodiments, the control (142) may control both the delivery of the insertion adapter (106) and the prosthesis (104) to the intervertebral disc space from the support (132) as well as the release of the insertion adapter (106) from the insertion tool body (130) following such delivery, but separate controls nay be provided for each function, and optionally may be provided for other functions. For insertion of the prosthesis (104) in various embodiments, the rod (136) may slide in the member (138) of the insertion tool body (130) toward the support (132) (the insertion direction), thus moving the insertion assembly (100) into the intervertebral disc space. With the insertion assembly (100) moved into the intervertebral disc space, threaded end (134) of rod (136) may be decoupled from the coupler of the insertion adapter (106) and the insertion tool body (103) moved away.

Various embodiments of the insertion tool body (130) may preferably be configured with an adjustable insertion stop to control the distance of the insertion of the intervertebral prosthesis (104) within the intervertebral disc space. FIGS. 6A, 6B, and 6C depict an exemplary adjustable stop configuration. In FIG. 6A, the prosthesis insertion assembly (100) is fully disposed in and firmly retained by support (132), with the threaded end (134) being substantially or fully engaged with threaded hole (140). A scale (147) may be disposed on a planar recess disposed on a shaft or stud (141) integral with or attached to the control knob (142). The scale (147) may be graduated in appropriate units of length and may include a zero mark (148). Tangs (164) and threaded hole (140) of insertion adapter (106) may be dimensioned and configured to accommodate further rotation of threaded end (134) in the threaded hole (140) in the position illustrated by FIG. 6A. Knob (142) may can be adjusted in handle (139) to position the zero mark (148) at an appropriate indicator, such as the end of handle (139) or other form of reference, for example as illustrated in FIG. 6B, which indexes knob (142), shaft or stud (141), rod (136), and the prosthesis insertion assembly (100) in the fully mounted position in support (132).

For various embodiments, when the zero mark (148) is set to the indicator with the prosthesis insertion assembly (100) in the fully mounted position in the support (132), for example as depicted in FIG. 6B, the scale (147) will indicate the distance that the prosthesis insertion assembly (100) has been extended from the support (132) by movement of the rod (136) within member (138) of insertion tool body (130). During the insertion of the intervertebral disc prosthesis (104), the leading edges (152) of the support (132) may be held firmly against respective vertebrae (150) defining the disc space receiving the prosthesis (104), as illustrated for example in FIGS. 8 and 10. Accordingly, the scale (147) can be used to indicate the distance of insertion of the prosthesis (104) within the intervertebral disc space.

Various embodiments may deploy an adjustable stop, for example a threaded nut (144) adjustable along threads (137) of the shaft or stud (141). The adjustable stop (144) may be used to control the distance of insertion of the prosthesis (104) within the intervertebral disc space. In various embodiments for example, sliding of the rod (136) in the insertion direction will be stopped when the adjustable stop (144) abuts the end of handle (139). A stop lock may be used to maintain the setting of the stop (144), for example by use of a lock nut (146) as illustrated, or by other known locking structures. Preferably, the stop (144) will be adjusted in accordance with the size of the intervertebral disc space, typically measured and analyzed before the insertion stage of the surgical procedure as discussed elsewhere in this disclosure. FIG. 6C depicts an insertion assembly (100) extended from support (132) by a distance controlled by stop (144) abutting handle (139).

Figure 7:
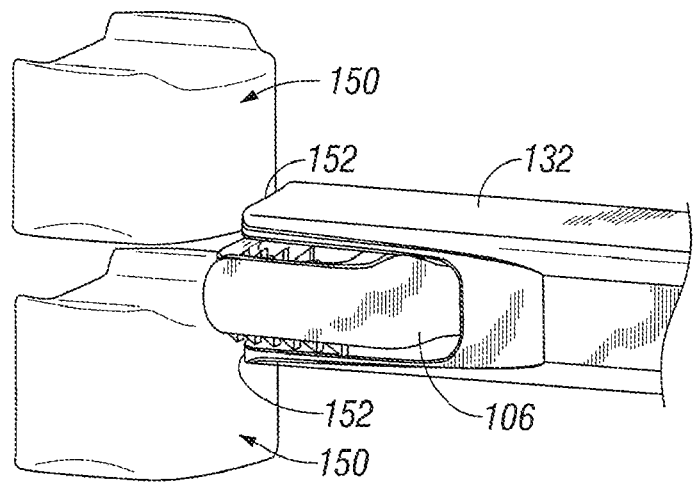
FIG. 7 depicts a prosthesis insertion assembly and a support of an insertion tool body.
Figure 8:
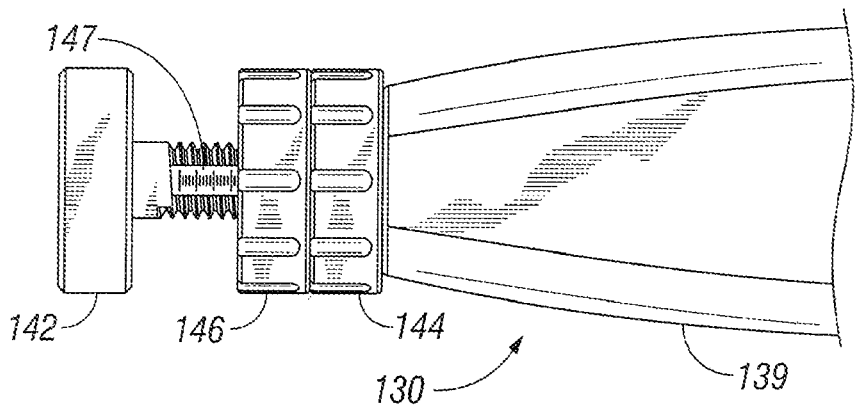
FIG. 8 depicts components and a portion of an insertion tool body.
Figure 9:
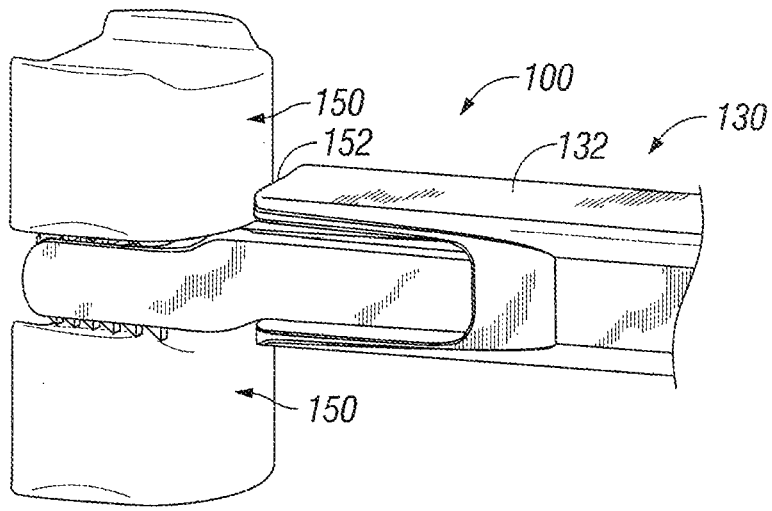
FIG. 9 depicts a prosthesis insertion assembly and a support of an insertion tool body.
Figure 10:
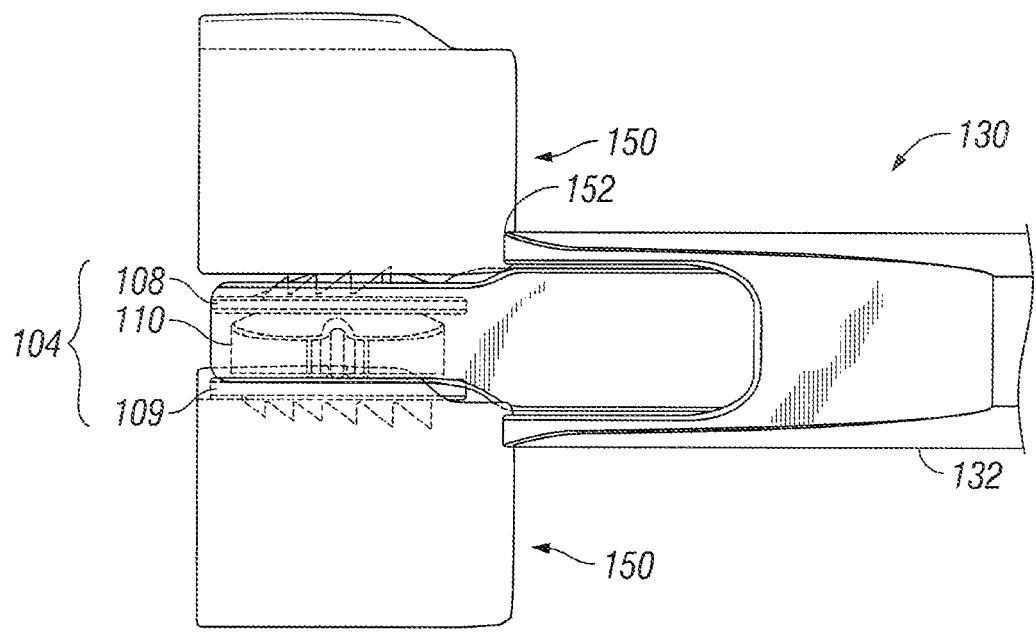
FIG. 10 depicts a prosthesis insertion assembly and a support of an insertion tool body.

FIG. 7 illustrates the commencement of the insertion stage of an embodiment of a surgical procedure. The insertion tool (130) and the prosthesis insertion assembly (100) may be configured and adjusted in accordance with the discussion above. The insertion tool (130) and the insertion assembly (100) may be located in the desired prosthesis insertion axis and located to place the leading edges (152) of the support (132) in contact with the respective vertebrae (150) defining the intervertebral disc space receiving the prosthesis (104). In various embodiment, the surgeon may apply force to the knob (142) by pressing it or striking it with a soft mallet or by hand. Force may be applied until the stop (144) abuts the end of the handle (139), as shown in FIG. 8. When the stop (144) abuts the end of the handle (139), the end (134) of the rod (136) will have pushed the insertion adapter (106) into position where the prosthesis (104) is properly positioned in the intervertebral disc space between the vertebrae (150). FIGS. 9 and 10 provide a representative illustration of the final positioning at this stage.

Figure 11:
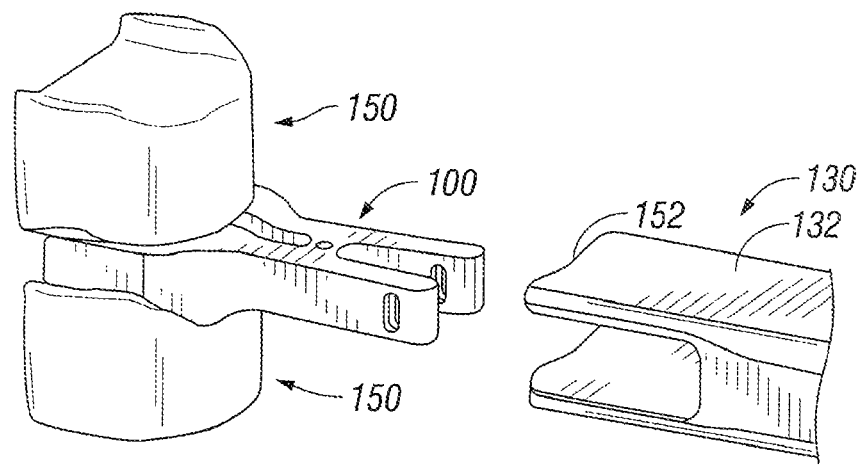
FIG. 11 depicts a prosthesis insertion assembly and a support of an insertion tool body.
Figure 12:
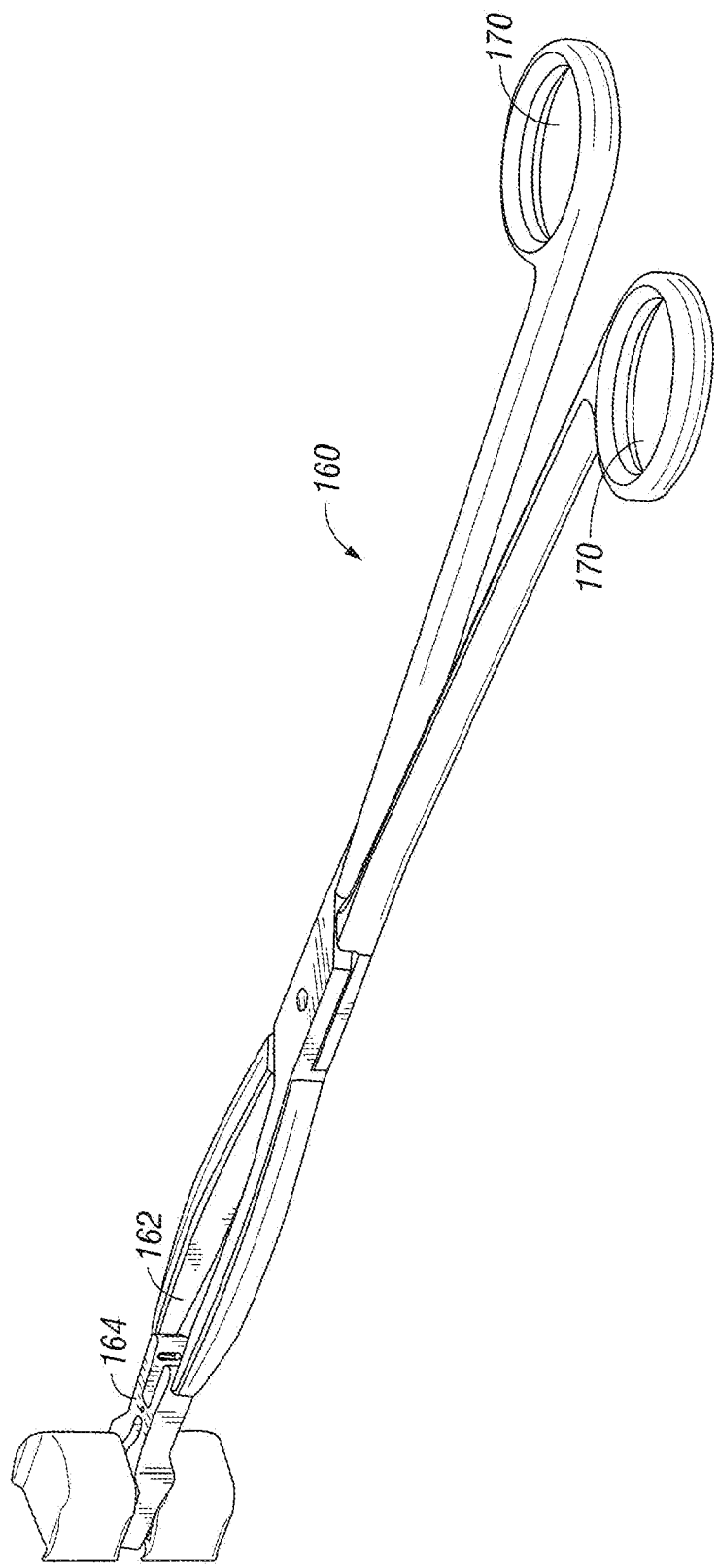
FIG. 12 depicts a removal tool.
Figure 13:
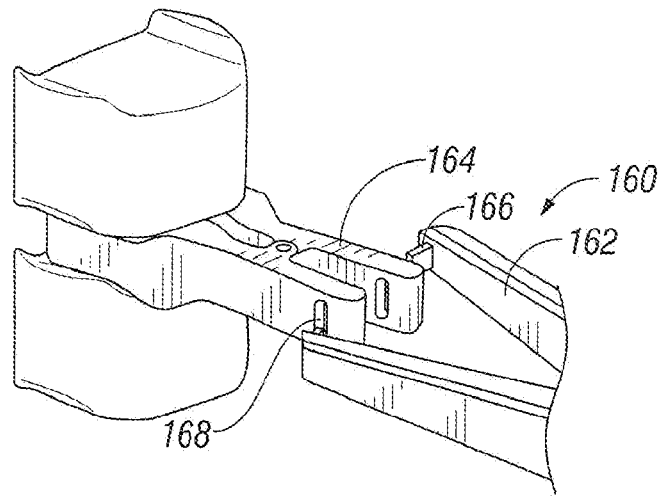
FIG. 13 depicts a prosthesis insertion assembly and a removal tool.
Figure 14:
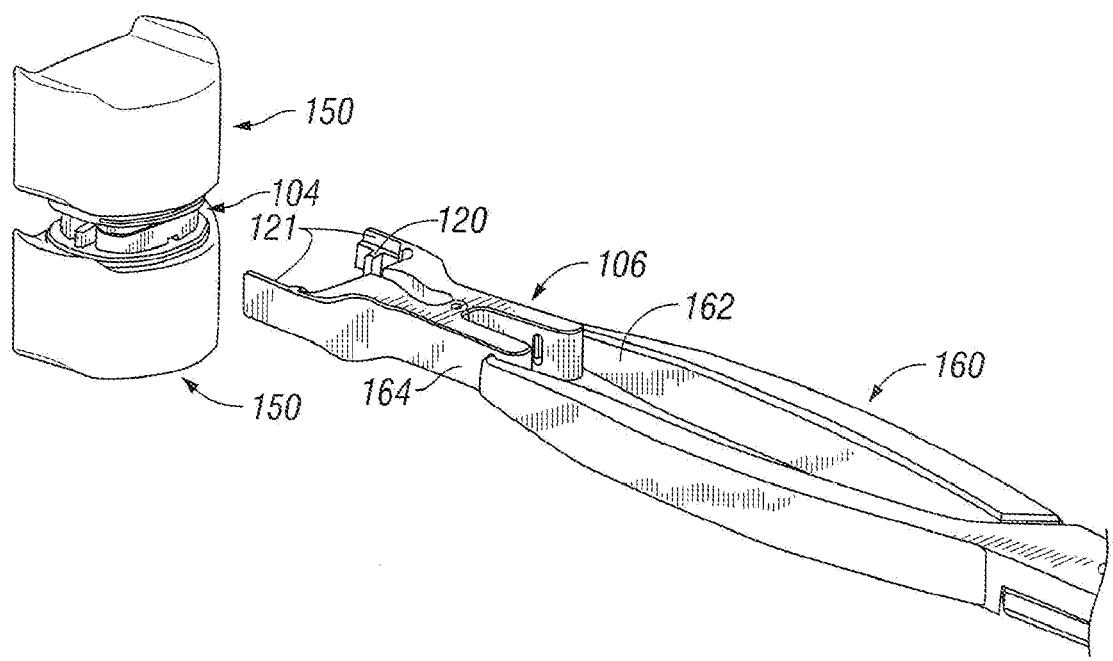
FIG. 14 depicts an intervertebral disc prosthesis, insertion adapter, and a removal tool.

For various embodiments, the insertion tool body (130) may be detached or demounted from the insertion assembly (100) by rotating the knob (142) counter-clockwise until the threaded end (134) releases from the threaded hole (140). FIG. 11 shows the insertion tool body (130) as it is being withdrawn, leaving only the insertion assembly (100) in the opening between the vertebrae (150). A removal tool (160), for example as shown in FIG. 12, may be used to separate the insertion adapter (106) from the prosthesis 104, leaving the prosthesis (104) implanted in the intervertebral disc space. FIG. 13 shows the removal tool (160) approaching the insertion adapter (106). Tool ends (162) of the removal tool (160) may be positioned along the tangs (164) of the insertion adapter (106) in such a way that pins (166) enter slots (168) disposed in the tangs (164). Other embodiments may include a single hole in each tang (164), multiple smaller holes or slots, or any of many other means for the removal tool (160) to attach with, connect to, or latch on the tangs (164) of the insertion adapter (106). Actuating a removal tool (160) by squeezing handles (170) of the removal tool (160) may pivot the tangs (164) of the insertion adapter (106) around the hinge pin (172), causing the jaws (121) to release the plates and the mounting dogs (120) to release their grip on the posts (124) and disengage from the recesses (122). In alternative embodiments of insertion adapter (106) comprising a flexible portion at which the tangs (164) articulate, squeezing the tangs (164) will cause the flexible body to flex, the tangs (164) to articulate, the jaws (121) to release the plates, and the mounting dogs (120) to release their rip on the posts (124) and disengage from the recesses (122). Once the insertion adapter (106) releases the prosthesis (104), the insertion adapter (106) may be removed, for example as shown in FIG. 14, leaving the prosthesis (104) properly positioned in the disc space between the two vertebrae (150).

Figure 15:
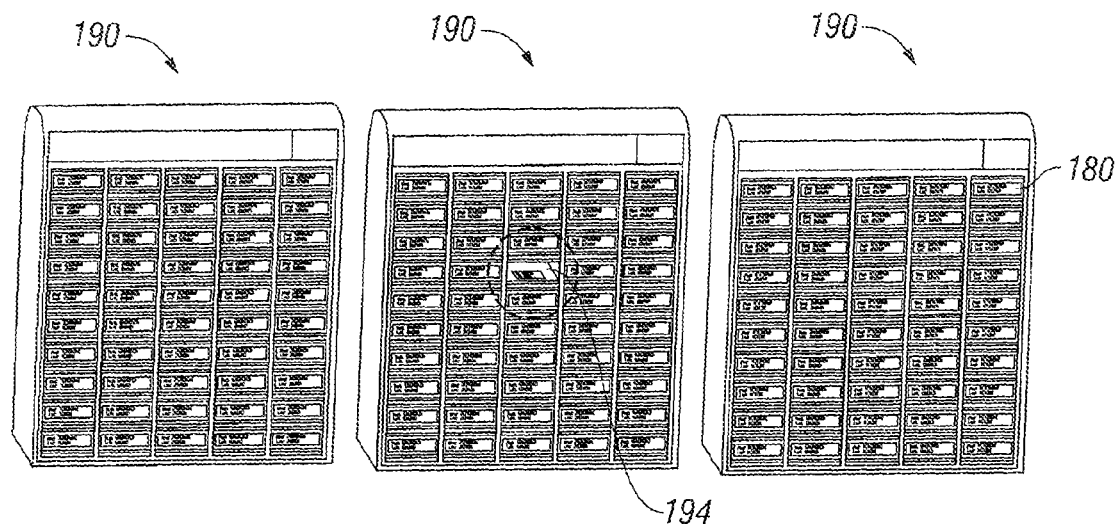
FIG. 15 depicts inventory storage space and a storage location.

Various embodiments of an intervertebral disc prosthesis delivery and insertion system also may be provided. In a preferred embodiment, the sterile pack (102) inventory may be maintained in dedicated inventory storage space, for example racks (190) as illustrated in FIG. 15. Various embodiments may have prostheses each configured with a first plate having a size and configuration selected from a set of first size and configuration specifications, a second plate having a size and configuration selected from a set of second size and configuration specifications, and a core having a size and configuration selected from a set of third size and configuration specifications. The first plate, the second plate, and/or the core configuration optionally may specify a lordosis or kyphosis correction. In various embodiments, any of the sets of size and configuration specifications may contain only one element, in which case the particular component may be provided in only one size and configuration.

Preferably, the inventory will be organized by plate dimension, core height, and lordosis/kyphosis correction angle (if any), but other characteristics of the prostheses (104) may be used for an organizational scheme. Each rack (190), for example, may contain insertion assemblies (100) of various dimensions all having a particular lordosis/kyphosis correction angle, with the sterile packs (102) organized in the respective racks (190) in rows by the plate dimension and in columns by the core height of the packaged prostheses (104). Alternatively, any organization scheme using any combination of the set of first size and configuration specifications, the set of second size and configuration specifications, and/or the third size and configuration specifications may be used. Preferably, each storage location (194) corresponds to one of the selected combinations of first size and configuration specifications, second size and configuration, specifications, and/or third size and configuration specifications.

As noted above, in various embodiments the sterile packs (102) of insertion assemblies (100) preferably bear identifying information. For example, various embodiments optionally have a package label with identifying information (180). The label (180) disposed on a sterile pack (102) preferably will indicate the enclosed prosthesis's plate dimension, core height, and lordosis/kyphosis correction angle (if any), along with the stock-keeping unit (SKU) designation of the sterile pack (102) and the other information discussed above, some or all of which preferably may be encoded in scannable code included on the label or other component of the packaging, for example a chip or transponder. Other information (180) optionally may be provided, for example further logistical management information such as inspection data, reorder points, lead times, etc., or information relevant to surgical techniques and equipment. Coding can be done with bar or other optical codes, magnetic stripes, radio-frequency identification, or other known techniques. The identifying information (180) on a sterile pack (102) preferably may be readable when insertion assembly (100) is stocked in the rack.

Figure 16:
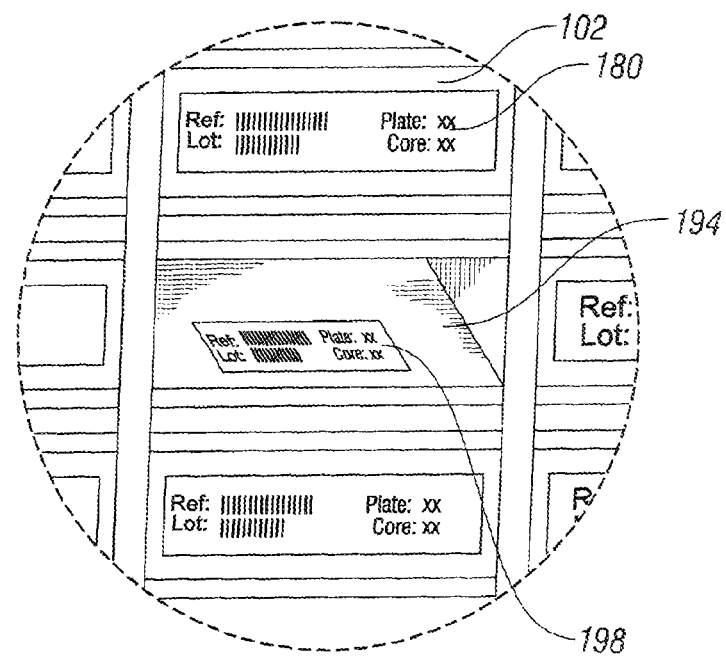
FIG. 16 depicts a storage location and configuration information.

The sterile pack (102) storage locations, for example binds (194) of the racks (190), optionally each may contain a label having identifying information for the sterile pack (102) that should be stocked in that bin (194), for example as depicted in FIG. 16. Other means of providing the information about the sterile pack (102) that should be stored in the bin (194), of course, may be use, for example magnetic stripes, radio-frequency identification, or other known techniques. Preferably, each bin label (194) or other form of identifying information may be readable when the respective bin (194) is empty. Thus, stock keeping may be simplified by providing sufficient information for re-ordering from routine observation of empty rack spaces, and acquisition of the correct assembly (100) during surgery may be simplified by the rack's organizational scheme. Stock keeping and insertion assembly (100) acquisition can be further enhanced by providing label- or other information-scanning equipment in the sterile field of the surgical suite, which will provide another level of verification of sterile pack (102) ordering and acquisition.

After appreciating this disclosure, those of skill in the art will recognize that other logistical management techniques advantageously can be applied to the intervertebral disc prosthesis delivery and insertion systems and methods disclosed herein.

Figure 17:
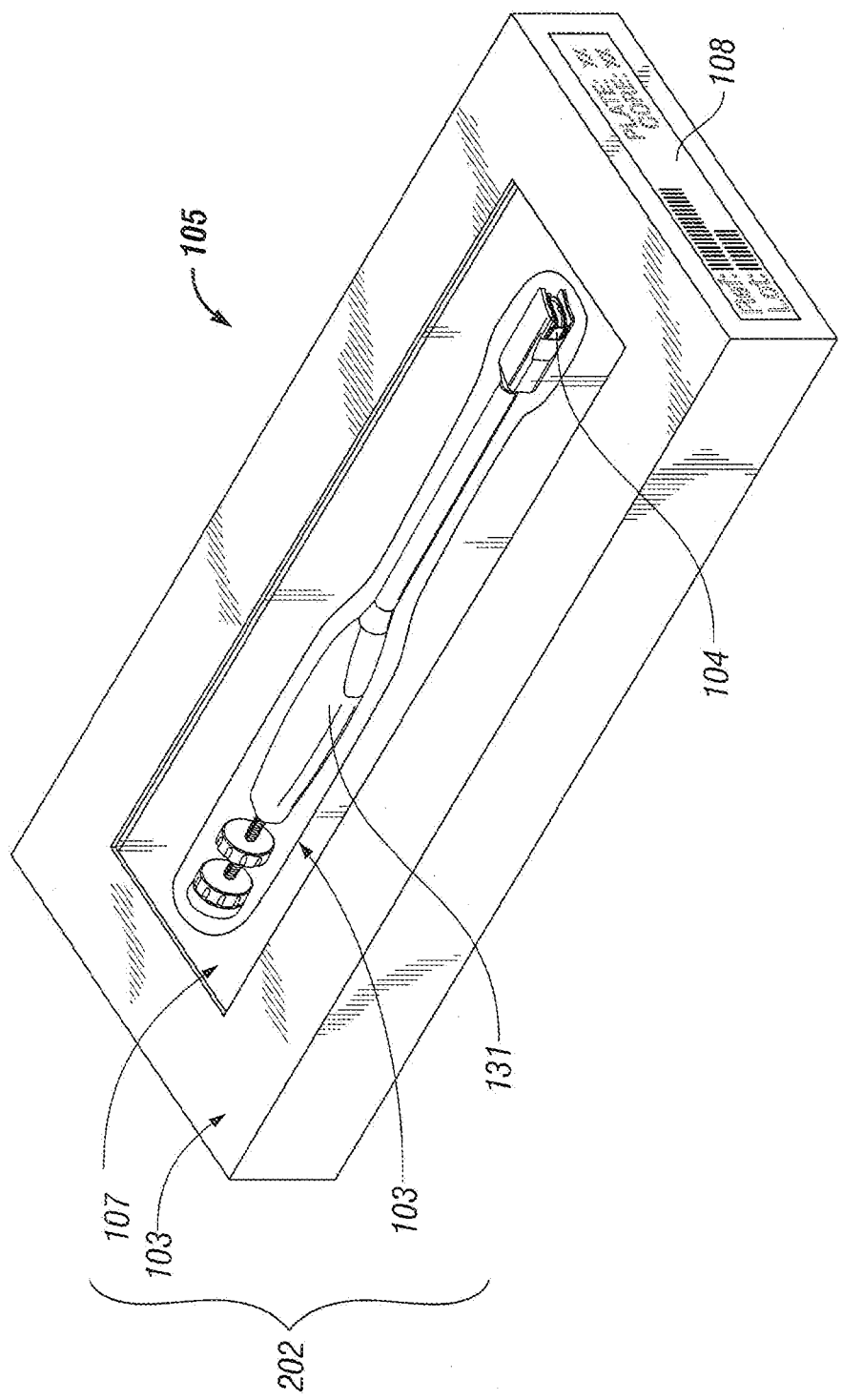
FIG. 17 depicts a sterile pack comprising a prosthesis insertion assembly.

Various features of embodiments of a packaged intervertebral disc prosthesis insertion assembly (101) comprising a sterile insertion adapter (106) and sterile components of an intervertebral disc prosthesis (104) are described above. Those of skill in the art will recognize after appreciating this disclosure that similar features may be provided in embodiments of a packaged intervertebral disc prosthesis insertion assembly (105) comprising a sterile insertion tool (131) and sterile components of an intervertebral disc prosthesis (104). For example, as shown in FIG. 17 the sterile insertion tool (131) and the sterile intervertebral disc prosthesis (104) may be assembled together and disposed in primary, or inner, sterile packaging (103) and in secondary, or outer, sterile packaging (103) to form a sterile pack (202). The components of the intervertebral disc prosthesis (104) in this embodiment may be assembled with the sterile insertion tool (131) and provided to the sterile field of a surgical suite pre-configured and ready to use. The sterile insertion tool (131) optionally may have an insertion tool body (130) and a detachable insertion adapter (106), which may be packaged assembled or disassembled. Alternatively, the sterile insertion tool (131) may have an insertion adapter (106) integral with an insertion tool body (130), or the sterile insertion tool (131) may have other structures devised to hold the intervertebral disc prosthesis (104) and/or deliver it to the intervertebral disc space. Various features of the insertion adapter (106) and/or the insertion tool body (130) discussed above, and/or the various components of the foregoing and other components discussed above, optionally may be included for the packaged intervertebral disc prosthesis insertion assembly (105). Various features the intervertebral disc prosthesis delivery and insertion systems discussed above, as well as features of other systems, optionally may also be used with a packaged intervertebral disc prosthesis insertion assembly (105) comprising a sterile insertion tool (131) and sterile components of an intervertebral disc prosthesis (104).

Those of skill in the art will recognize after appreciating this disclosure that the steps of the various methods, processes, and other techniques disclosed herein need not be performed in any particular order, unless otherwise expressly stated or logically necessary to satisfy expressly stated antecedent conditions. In addition, after appreciating this disclosure those skilled in the art will recognize that the invention may be embodied in a variety of different forms and that various changes, substitutions, and alterations can be made without departing from the spirit and scope of the invention. The described embodiments are illustrative only and are not restrictive, and the scope of the invention is defined solely by the following claims.

The invention claimed is:

1. A method of inserting an intervertebral disc prosthesis between adjacent elements of a spinal column, the method comprising the steps of:
    providing an actuateable insertion adapter and an intervertebral disc prosthesis;
    mounting the intervertebral disc prosthesis to the insertion adapter to form an insertion assembly;
    providing an insertion tool body;
    mounting the insertion assembly to the insertion tool body;
    inserting the intervertebral disc prosthesis between adjacent elements of a spinal column; and
    demounting the intervertebral disc prosthesis from the insertion assembly.

2. A method of inserting an intervertebral disc prosthesis according to claim 1, comprising the step of demounting the insertion adapter from the insertion tool body and discarding the insertion adapter.

3. A method of inserting an intervertebral disc prosthesis between adjacent elements of a spinal column, the method comprising the steps of:
    providing an actuateable insertion adapter and components of an intervertebral disc prosthesis;
    assembling the components of the intervertebral disc prosthesis and the insertion adapter to form an insertion assembly;
    providing an insertion tool body;
    assembling the insertion assembly and the insertion tool body;
    placing the intervertebral disc prosthesis between adjacent elements of a spinal column; and
    removing the intervertebral disc prosthesis from the insertion assembly.

4. The method of claim 3 in which the step of providing an actuateable insertion adapter and components of an intervertebral disc prosthesis comprises the steps of:
    packaging the components of the intervertebral disc prosthesis and the insertion adapter in sterile packaging to form a sterile pack; and then
    transporting the sterile pack to a sterile field.

5. The method of claim 3 further comprising the steps of:
    packaging the insertion assembly in sterile packaging to form a sterile pack; and then
    transporting the sterile pack to a sterile field.

6. A method of aseptically delivering an intervertebral disc prosthesis insertion assembly to a sterile field, the method comprising the steps of:
 providing sterile components of an intervertebral disc prosthesis and a sterile actuateable insertion adapter having an operationally releasable coupler for a detachable insertion tool body;
 packaging the components of the intervertebral disc prosthesis and the insertion adapter into sterile packaging to form a primary sterile pack;
 transporting the sterile pack containing the intervertebral disc prosthesis and the insertion adapter into a sterile field; and
 removing the intervertebral disc prosthesis and the insertion adapter from the sterile pack within the sterile field.

7. The method of claim 6 further comprising, prior to the step of packaging, the step of assembling the components of the intervertebral disc prosthesis and the insertion adapter.

8. The method of claim 6 further comprising the step of packaging the primary sterile pack into a secondary sterile pack.

9. A method of inserting an intervertebral disc prosthesis between adjacent elements of a spinal column, the method comprising the steps of:
 acquiring an actuateable insertion adapter and an intervertebral disc prosthesis;
 mounting the intervertebral disc prosthesis to the insertion adapter to form an insertion assembly;
 acquiring an insertion tool body;
 mounting the insertion assembly to the insertion tool body;
 inserting the intervertebral disc prosthesis between adjacent elements of a spinal column; and
 demounting the intervertebral disc prosthesis from the insertion assembly.

10. The method of claim 9, further comprising the step of demounting the insertion adapter from the insertion tool body and discarding the insertion adapter.

11. A method of inserting an intervertebral disc prosthesis between adjacent elements of a spinal column, the method comprising the steps of:
 acquiring an actuateable insertion adapter and components of an intervertebral disc prosthesis with the components of the intervertebral disc prosthesis and the insertion adapter pre-assembled to form an insertion assembly;
 acquiring an insertion tool body;
 assembling the insertion assembly and the insertion tool body;
 placing the intervertebral disc prosthesis between adjacent elements of a spinal column; and
 removing the intervertebral disc prosthesis from the insertion assembly.

12. The method of claim 11 in which the insertion assembly is packaged in sterile packaging to form a sterile pack, and further comprising the step of receiving the sterile pack within a sterile field.

13. The method of claim 11 further comprising the step of discarding the insertion adapter.

* * * * *